US008354518B2

(12) United States Patent
Ludmerer et al.

(10) Patent No.: US 8,354,518 B2
(45) Date of Patent: Jan. 15, 2013

(54) HCV REPLICONS CONTAINING NS5B FROM GENOTYPE 2B

(75) Inventors: Steven W. Ludmerer, North Wales, PA (US); Donald J. Graham, Green Lane, PA (US); Robert L. LaFemina, Schwenksville, PA (US); Osvaldo A. Flores, North Wales, PA (US); Maura Pizzuti, Rome (IT); Cinzia Traboni, Rome (IT)

(73) Assignees: Merck Sharp & Dohme Corp., Rahway, NJ (US); Istituto di Richerche di Biologia Molecolare P. Angeletti S.p.A., Rome (IT)

( * ) Notice: Subject to any disclaimer, the term of this patent is extended or adjusted under 35 U.S.C. 154(b) by 1807 days.

(21) Appl. No.: 10/577,893

(22) PCT Filed: Nov. 3, 2004

(86) PCT No.: PCT/US2004/036575
§ 371 (c)(1),
(2), (4) Date: May 1, 2006

(87) PCT Pub. No.: WO2005/047463
PCT Pub. Date: May 26, 2005

(65) Prior Publication Data
US 2011/0250628 A1    Oct. 13, 2011

Related U.S. Application Data

(60) Provisional application No. 60/517,605, filed on Nov. 5, 2003.

(51) Int. Cl.
C07H 21/04       (2006.01)
C12P 21/00       (2006.01)
C12N 15/00       (2006.01)
C12N 7/00        (2006.01)
(52) U.S. Cl. .................. 536/23.72; 435/69.1; 435/235.1
(58) Field of Classification Search .................. None
See application file for complete search history.

(56) References Cited

U.S. PATENT DOCUMENTS

| 6,383,768 | B1 | 5/2002 | De Francesco et al. |
| 6,630,343 | B1 | 10/2003 | Bartenschlager |
| 2003/0028011 | A1 | 2/2003 | Parkin et al. |

FOREIGN PATENT DOCUMENTS

| WO | WO 01/89364 A3 | 11/2001 |
| WO | WO 02/38793 A3 | 5/2002 |
| WO | WO 02/052015 A2 | 7/2002 |
| WO | WO 02/059321 A2 | 8/2002 |

OTHER PUBLICATIONS

Baohua, Gu., et al, "Replication Studies Using Genotype 1a Subgenomic Hepatitis C Virus Replicons", Journal of Virology, May 2003, p. 5352-5359, vol. 77, No. 9.

Lohmann, V., et al "Mutations in Hepatitis C Virus RNAs Conferring Cell Culture Adaptation", Journal of Virology, Feb. 2001, p. 1437-1449, vol. 75, No. 3.
Cheney, W., et al "Mutations in NS5B Polymerase of Hepatitis C Virus: Impacts on in Vitro Enzymatic Activity and Viral RnA Replication in the Subgenomic Replicon Cell Culture", Virology, 2002, p. 298-306, vol. 297.
Graham, D.J., et al "A Genotype 2b NS5B Polymerase With Novel Substitutions Supports Replication of a Chimeric HCV 1b:2b Replicon Containing a Genotype 1B NS3-5A Background", Antiviral Research, 2006, p. 24-30, vol. 69.
Bartenschlager, R. "Hepatitis C virus replicons: potential role for drug development", Nature Reviews, 2002, vol. 1, pp. 911-916.
Bartenschlager, R. et al. "Nonstructural Protein 3 of the Hepatitis C Virus Encodes a Serine-Type Proteinase Required for Cleavage at the NS3/4 adn NS4/5 Junctions", Journal of Virology, 1993, vol. 67, pp. 3835-3844.
Behrens, S. et al. "Identification and properties of the RNA-dependent RNA polymerase of hepatitis C virus", The EMBO Journal, 1996, vol. 15, pp. 12-22.
Blight, K. et al. "Efficient Initiation of HCV RNA Replication in Cell Culture", Science, 2000, vol. 290, pp. 1972-1974.
Carroll, S. et al. "Inhibition of Hepatitis C Virus RNA Replication by 2'-Modified Nucleoside Analogs", The Journal of Biological Chemistry, 2003, vol. 278, pp. 11979-11984.
Choo, Q. et al. "Isolation of a cDNA Clone Derived from a Blood-Borne Non-A, Non-B Viral Hepatitis Genome", Sciene, 1989, vol. 244, pp. 359-362.
Farci, P. et al. "Clinical Significance of Hepatitis C Virus Genotypes and Quasispecies", Seminars in Liver Disease, 2000, vol. 20, pp. 103-126.
Grakoui, A. et al. "A second hepatitis C virus-encoded proteinase", Proc. Natl. Acad. Sci. USA, 1993, vol. 90, pp. 10583-10587.
Grakoui, A. et al. "Expression and Identification of Hepatitis C Virus Polyprotein Cleavage Products", Journal of Virology, 1993, vol. 67, pp. 1385-1395.
Grobler, J. et al. "Identification of Key Determinant of Hepatitis C Virus Cell Culture Adaptation in Domain II of NS3 Helicase", The Journal of Biological Chemistry, 2003, vol. 278, pp. 16741-16746.
Hijikata, M. et al. Proteolytic processing and membrane association of putative nonstructural proteins of hepatitis C virus, Proc. Natl. Acad. Sci. USA, 1993, vol. 90, pp. 10773-10777.

(Continued)

*Primary Examiner* — Louise Humphrey
(74) *Attorney, Agent, or Firm* — Melissa B. Wenk; Sheldon O. Heber

(57) ABSTRACT

The present invention features methods for enhancing the ability of a genotype 2b NS5B sequence to function in a replicon, for producing replicons containing a functional genotype 2b NS5B, and for using replicons to measure the ability of a compound to affect HCV replication that is sustained with the genotype 2b polymerase. Also featured is a genotype 1b NS4B adaptive mutation. The ability to produce replicons containing a functional genotype 2b NS5B is illustrated by the production of chimeric replicons based on HCV genotype 1b where substantially all the NS5B sequence is replaced with a genotype 2b NS5B.

20 Claims, 7 Drawing Sheets

OTHER PUBLICATIONS

Ikeda, M. et al. "Selectable Subgenomic and Genome-Length Dicistronic RNAs Derived from an Infectious Molecular Cone of the HCV-N Strain of Hepatitis C Virus Replicate Efficiently in Cultured Huh7 Cells", Journal of Virology, 2002, vol. 76, pp. 2997-3006.

Krieger, N. et al. "Enhancement of Hepatitis C Virus RNA Replication by Cell Culture-Adaptive Mutations", Journal of Virology, 2001, vol. 75. pp. 4614-4624.

Kuo, G. et al. "An Assay for Circulating Antibodies to a Major Etiologic Virus of Human Non-A, Non-B Hepatitis", Science, 1989, vol. 244, pp. 362-364.

Lohmann, V. et al. "Biochemical and Kinetic Analyses of NS5B RNA-Dependent RNA Polymerase of the Hepatitis C Virus", Virology, 1998, vol. 249, pp. 108-118.

Lohmann, V. et al. "Mutations in Hepatitis C Virus RNAs Conferring Cell Culture Adaptation" Journal of Virology, 2001, vol. 75, pp. 1437-1449.

Lohmann, V. et al. "Replication of Subgenomic Hepatitis C Virus RNAs in a Hepatoma Cell Line", Science, 1999, vol. 285, pp. 110-113.

Lohmann, V. et al. "Viral and Cellular Determinants of Hepatitis C Virus RNA Replication in Cell Culture", Journal of Virology, 2003, vol. 77, pp. 2007-3019.

Love, R. et al. "Crystallographic Identification of a Noncompetitive Inhibitor Binding Site on the Hepatitis C Virus NS5B RNA Polymerase Enzyme", Journal of Virology, 2003, vol. 77, pp. 7575-7581.

Mizushima, H. et al. "Analysis of N-Terminal Processing of Hepatitis C Virus Nonstructural Protein 2", Journal of Virology, 1994, vol. 68, pp. 2731-2734.

Murray, E. et al. "Persistent Replication of Hepatitis C Virus Replicons Expressing the B-Lactamase Reporter in Subpopulations of Highly Permissive Huh7 Cells", Journal of Virology, 2003, vol. 77, pp. 2928-2935.

Pawlotsky, J. et al. "Hepatitis C virus (HCV) NS5A protein; role in HCV replication and resistance to interferon $\alpha$", Journal of Viral Hepatitis, 1999, vol. 6, pp. 47-48.

Pietschmann, T. et al. "Characterization of Cell Lines Carrying Self-Replicating Hepatitis C Virus RNAs", Journal of Virology, 2001, vol. 75, pp. 1252-1264.

Takamizawa, A. et al. "Structure and Organization of the Hepatitis C Virus Genome Isolated from Human Cariers", Journal of Virology, 1991, vol. 65, pp. 1105-1113.

Tomei, L. et al."Mechanism of Action and Antiviral Activity of Benzimidazole-Based Allosteric Inhibitors of the Hepatitis C Virus RNA-Dependent RNA Polymerase", 2003, vol. 77, pp. 13225-13231.

Tomei, L. et al. "NS3 Is a Serine Protease Required for Processing of Hepatitis C Virus Polyprotein", Journal of Virology, 1993, vol. 67, pp. 4017-4026.

Vrolijk, J. et al. "A replicon-based bioassay for the measurement of interferons in patients with chronic hepatitis C", Journal of Virological Methods, 2003, vol. 110, pp. 201-209.

Wang, M. et al. "Non-nucleoside Analogue Inhibitors Bind to an Allosteric Site on HCV NS5B Polymerase", The Journal of Biological Chemistry, 2003, vol. 278, pp. 9489-9495.

SMSYZ¹WTGALITPCGPEEEKLPIX¹PLSNSLX²RFHNKVYSTTSRSASLRAKKVTFDRVQV
LDAHYDSVLQDVKRAASKVSARLLTVEEACALTPPHSAKSRYGFGAKEVRSLSRRAVNHIR
SVWEDLLEDQHTPIDTTIMAKNEVFCIDPTKGGKKPARLIVYPDLGVRVCEKMALYDIAQK
LPKAIMGPSYGFQYSPAERVDFLLKAWGSKKDPMGFSYDTRCFDSTVTERDIRTEESIYQA
CSLPQEARTVIHSLTERLYVGGPMTNSKGQSCGYRRCRASGVFTTSMGNTMTCYIKALAAC
KAAGIVDPVMLVCGDDLVVISESQGNEEDERNLRAFTEAMTRYSAPPGDLPRPEYDLELIT
SCSSNVSVALDSRGRRRYFLTRDPTTPX³TRAAWETVRHSPVNSWLGNIIQYAPTIWVRMVI
MTHFFSILLAQDTLNQNLNFEMYGAVYSVNPLDLPAIIERLHGLEAFSLHTYSPHELSRVA
ATLRKLGAPPLRAWKSRARAVRASLIAQGARAAICGRYLFNWAVKTKLKLTPLPEASRLDL
SGWFTVGAGGGDIYHSVSHARPRLLLLCLLLLSVGVGIFLLPDR

FIG. 1

TC$\mathbf{Y}^1$ATGTC$\mathbf{Y}^2$TAC$\mathbf{Y}^3$C$\mathbf{Y}^4$TGGAC$\mathbf{Y}^5$GG$\mathbf{Y}^6$GCC$\mathbf{Y}^7$T$\mathbf{Y}^8$AT$\mathbf{Y}^9$ACACCATGTGGGCCCGAAGAGG
AGAAGTTACCGATCA$\mathbf{X}^1$CCCTCTGAGTAATTCGCTCAT$\mathbf{X}^2$CGGTTCCATAATAAGGTGTACT
CCACAACCTCGAGGAGTGCCTCTCTGAGGGCAAAGAAGGTGACTTTTGACAGGGTGCAGGT
GCTGGACGCACACTATGACTCAGTCTTGCAGGACGTTAAGCGGGCCGCCTCTAAGGTTAGT
GCGAGGCTCCTCACGGTAGAGGAAGCCTGCGCGCTGACCCCGCCCCACTCCGCCAAATCGC
GATACGGATTTGGGGCAAAAGAGGTGCGCAGCTTATCTAGGAGGGCCGTTAACCACATCCG
GTCCGTGTGGGAGGACCTCCTGGAAGACCAACATACCCCAATTGACACAACTATCATGGCT
AAAAATGAGGTGTTCTGCATTGATCCAACTAAAGGTGGAAAAAGCCAGCTCGCCTCATCG
TATACCCCGACCTTGGGGTCAGGGTGTGCGAAAAGATGGCCCTCTATGACATCGCACAAAA
GCTTCCCAAAGCGATAATGGGGCCATCCTATGGGTTCCAATACTCTCCCGCAGAACGGGTC
GATTTCCTCCTCAAAGCTTGGGGAAGTAAGAAGGACCCAATGGGGTTCTCGTATGACACCC
GCTGCTTTGACTCAACCGTCACGGAGAGGGACATAAGAACAGAAGAATCCATATATCAGGC
TTGTTCTCTGCCTCAAGAAGCCAGAACTGTCATACACTCGCTCACTGAGAGACTTTACGTA
GGAGGGCCCATGACAAACAGCAAAGGGCAATCCTGCGGCTACAGGCGTTGCCGCGCAAGCG
GTGTTTTCACCACCAGCATGGGGAATACCATGACATGTTACATCAAAGCCCTTGCAGCGTG
TAAGGCTGCAGGGATCGTGGACCCTGTTATGTTGGTGTGTGGAGACGACCTGGTCGTCATC
TCAGAGAGCCAAGGTAACGAGGAGGACGAGCGAAACCTGAGAGCTTTCACGGAGGCTATGA
CCAGGTATTCCGCCCCTCCCGGTGACCTTCCCAGACCGGAATATGACTTGGAGCTTATAAC
ATCCTGCTCCTCAAACGTATCGGTAGCGCTGGACTCTCGGGGTCGCCGCCGGTACTTCCTA
ACCAGAGACCCTACCACTCCA$\mathbf{X}^3$TCACCCGAGCTGCTTGGGAAACAGTAAGACACTCCCCTG
TCAATTCTTGGCTGGGCAACATCATCCAGTACGCCCCCACAATCTGGGTCCGGATGGTCAT
AATGACTCACTTCTTCTCCATACTATTGGCCCAGGACACTCTGAACCAAAATCTCAATTTT
GAGATGTACGGGGCAGTATACTCGGTCAATCCATTAGACCTACCGGCCATAATTGAAAGGC
TACATGGGCTTGAAGCCTTTTCACTGCACACATACTCTCCCCACGAACTCTCACGGGTGGC
AGCAACTCTCAGAAAACTTGGAGCGCCTCCCCTTAGAGCGTGGAAGAGTCGGGCGCGTGCC
GTGAGAGCTTCACTCATCGCCCAAGGAGCGAGGGCGGCCATTTGTGGCCGCTACCTCTTCA
ACTGGGCGGTGAAAACAAAGCTCAAACTCACTCCATTGCCCGAGGCGAGCCGCCTGGATTT
ATCCGGGTGGTTCACCGTGGGCGCCGGCGGGGGCGACATTTATCACAGCGTGTCGCATGCC
CGACCCCGCCTATTACTCCTTTGCCTACTCCTACTTAGCGTAGGAGTAGGCATCTTTTTAC
TCCCCGATCGATGA

FIG. 2

```
MAPITAYSQQTRGLLGCIITSLTGRDKNQVEGEVQVVSTATQSFLATCVNGVCWTVYHGAG
SKTLAGPKGPITQMYTNVDQDLVGWQAPPGARSLTPCTCGSSDLYLVTRHADVIPVRRRGD
SRGSLLSPRPVSYLKGSSGGPLLCPSGHAVGIFRAAVCTRGVAKAVDFVPVESMETTMRSP
VFTDNSSPPAVPQTFQVAHLHAPTGSGKSTKVPAAYAAQGYKVLVLNPSVAATLGFGAYMS
KAHGIDPNIRTGVRTITTGAPVTYSTYGKFLADGGCSGGAYDIIICDECHSTDSTTILGIG
TVLDQAETAGARLVVLATATPPGSVTVPHPNIEEVALSNTGEIPFYGKAIPIEAIRGGRHL
IFCHSKKKCDELAAKLSGLGINAVAYYRGLDVSVIPTIGDVVVVATDALMTGYTGDFDSVI
DCNTCVTQTVDFSLDPTFTIETTTVPQDAVSRSQRRGRTGRGRMGIYRFVTPGERPSGMFD
SSVLCECYDAGCAWYELTPAETSVRLRAYLNTPGLPVCQDHLEFWESVFTGLTHIDAHFLS
QTKQAGDNFPYLVAYQATVCARAQAPPPSWDQMWKCLIRLKPTLHGPTPLLYRLGAVQNEV
TLTHPITKYIMACMSADLEVVTSTWVLVGGVLAALAAYCLTTGSVVIVGRIILSGRPAIVP
DREFLYQEFDEMEECASHLPYIEQGMQLAEQFKQKALGLLQTATKQAEAAAPVVESKWRAL
ETFWAKHMWNFISGIQYLAGLSTLPGNPAIASLMAFTASITSPLTTQSTLLFNILGGWVAA
QLAPPSAASAFVGAGIAGAAVGSIGLGKVLVDILAGYGAGVAGALVAFKVMSGEMPSTEDL
VNLLPAILSPGALVVGVVCAAILRRHVGPGEGAVQWMNRLIAFASRGNH$X^2$SPTHYVPESDA
AARVTQILSSLTITQLLKRLHQWINEDCSTPCSGSWLRDVWDWICTVLTDFKTWLQSKLLP
QLPGVPFFSCQRGYKGVWRGDGIMQTTCPCGAQITGHVKNGSMRIVGPKTCSNTWHGTFPI
NAYTTGPCTPSPAPNYSRALWRVAAEEYVEVTRVGDFHYVTGMTTDNVKCPCQVPAPEFFT
EVDGVRLHRYAPACRPLLREEVTFQVGLNQYLVGSQLPCEPEPDVAVLTSMLTDPSHITAE
TAKRRLARGSPPSLASSSAIQLSAPSLKATCTTHHVSPDADLIEANLLWRQEMGG$X^1$ITRVE
SENKVVVLDSFDPLRAEEDEREVSVPAEILRKSKKFPAAMPIWARPDYNPPLLESWKDPDY
VPPVVHGCPLPPIKAPPIPPPRRKRTVVLTESSVSSALAELATKTFGSSESSAVDSGTATA
LPDQASDDGDKGSDVESYSSMPPLEGEPGDPDLSDGSWSTVSEEASEDVVCC
```

FIG. 3

```
ATGGCGCCCATCACGGCCTACTCCCAACAGACGCGGGGCCTACTTGGTTGCATCATCACTA
GCCTTACAGGCCGGGACAAGAACCAGGTCGAGGGAGAGGTTCAGGTGGTTTCCACCGCAAC
ACAATCCTTCCTGGCGACCTGCGTCAACGGCGTGTGTTGGACCGTTTACCATGGTGCTGGC
TCAAAGACCTTAGCCGGCCCAAAGGGGCCAATCACCCAGATGTACACTAATGTGGACCAGG
ACCTCGTCGGCTGGCAGGCGCCCCCGGGGCGCGTTCCTTGACACCATGCACCTGTGGCAG
CTCAGACCTTTACTTGGTCACGAGACATGCTGACGTCATTCCGGTGCGCCGGCGGGGCGAC
AGTAGGGGGAGCCTGCTCTCCCCAGGCCTGTCTCCTACTTGAAGGGCTCTTCGGGTGGTC
CACTGCTCTGCCCTTCGGGGCACGCTGTGGGCATCTTCCGGGCTGCCGTATGCACCCGGGG
GGTTGCGAAGGCGGTGGACTTTGTGCCCGTAGAGTCCATGGAAACTACTATGCGGTCTCCG
GTCTTCACGGACAACTCATCCCCCCGGCCGTACCGCAGACATTTCAAGTGGCCCACCTAC
ACGCTCCCACTGGCAGCGGCAAGAGTACTAAAGTGCCGGCTGCATATGCAGCCCAAGGGTA
CAAGGTGCTCGTCCTCAATCCGTCCGTTGCCGCTACCTTAGGGTTTGGGGCGTATATGTCT
AAGGCACACGGTATTGACCCCAACATCAGAACTGGGGTAAGGACCATTACCACAGGCGCCC
CCGTCACATACTCTACCTATGGCAAGTTTCTTGCCGATGGTGGTTGCTCTGGGGGCGCTTA
TGACATCATAATATGTGATGAGTGCCATTCAACTGACTCGACTACAATCTTGGGCATCGGC
ACAGTCCTGGACCAAGCGGAGACGGCTGGAGCGCGGCTTGTCGTGCTCGCCACCGCTACGC
CTCCGGGATCGGTCACCGTGCCACACCCAAACATCGAGGAGGTGGCCCTGTCTAATACTGG
AGAGATCCCCTTCTATGGCAAAGCCATCCCCATTGAAGCCATCAGGGGGGGAAGGCATCTC
ATTTTCTGTCATTCCAAGAAGAAGTGCGACGAGCTCGCCGCAAAGCTGTCAGGCCTCGGAA
TCAACGCTGTGGCGTATTACCGGGGGCTCGATGTGTCCGTCATACCAACTATCGGAGACGT
CGTTGTCGTGGCAACAGACGCTCTGATGACGGGCTATACGGCGACTTTGACTCAGTGATC
GACTGTAACACATGTGTCACCCAGACAGTCGACTTCAGCTTGGATCCCACCTTCACCATTG
AGACGACGACCGTGCCTCAAGACGCAGTGTCGCGCTCGCAGCGGCGGGGTAGGACTGGCAG
AGGTAGGATGGGCATCTACAGGTTTGTGACTCCGGGAGAACGGCCCTCGGGCATGTTCGAT
TCCTCGGTCCTGTGTGAGTGCTATGACGCGGGCTGTGCTTGGTACGAGCTCACCCCCGCCG
AGACCTCGGTTAGGTTGCGGGCCTACCTGAACACACCAGGGTTGCCCGTTTGCCAGGACCA
CCTGGAGTTCTGGGAGAGTGTCTTCACAGGCCTCACCCACATAGATGCACACTTCTTGTCC
CAGACCAAGCAGGCAGGAGACAACTTCCCCTACCTGGTAGCATACCAAGCCACGGTGTGCG
CCAGGGCTCAGGCCCCACCTCCATCATGGGATCAAATGTGGAAGTGTCTCATACGGCTGAA
ACCTACGCTGCACGGGCCAACACCCTTGCTGTACAGGCTGGGAGCCGTCCAAAATGAGGTC
ACCCTCACCCACCCCATAACCAAATACATCATGGCATGCATGTCGGCTGACCTGGAGGTCG
TCACTAGCACCTGGGTGCTGGTGGGCGGAGTCCTTGCAGCTCTGGCCGCGTATTGCCTGAC
AACAGGCAGTGTGGTCATTGTGGGTAGGATTATCTTGTCCGGGAGGCCGGCTATTGTTCCC
GACAGGGAGTTTCTCTACCAGGAGTTCGATGAAATGGAAGAGTGCGCCTCGCACCTCCCTT
ACATCGAGCAGGGAATGCAGCTCGCCGAGCAATTCAAGCAGAAAGCGCTCGGGTTACTGCA
AACAGCCACCAAACAAGCGGAGGCTGCTGCTCCCGTGGTGGAGTCCAAGTGGCGAGCCCTT
GAGACATTCTGGGCGAAGCACATGTGGAATTTCATCAGCGGGATACAGTACTTAGCAGGCT
TATCCACTCTGCCTGGGAACCCCGCAATAGCATCATTGATGGCATTCACAGCCTCTATCAC
CAGCCCGCTCACCACCCAAAGTACCCTCCTGTTTAACATCTTGGGGGGTGGGTGGCTGCC
CAACTCGCCCCCCCCAGCGCCGCTTCGGCTTTCGTGGGCGCCGGCATCGCCGGTGCGGCTG
TTGGCAGCATAGGCCTTGGGAAGGTGCTTGTGGACATTCTGGCGGGTTATGGAGCAGGAGT
GGCCGGCGCGCTCGTGGCCTTCAAGGTCATGAGCGGCGAGATGCCCTCCACCGAGGACCTG
GTCAATCTACTTCCTGCCATCCTCTCTCCTGGCGCCCTGGTCGTCGGGGTCGTGTGTGCAG
CAATACTGCGTCGACACGTGGGTCCGGGAGAGGGGCTGTGCAGTGGATGAACCGGCTGAT
AGCGTTCGCCTCGCGGGTAATCATG$x^2$TTCCCCCACGCACTATGTGCCTGAGAGCGACGCC
GCAGCGCGTGTTACTCAGATCCTCTCCAGCCTTACCATCACTCAGCTGCTGAAAAGGCTCC
ACCAGTGGATTAATGAAGACTGCTCCACACCGTGTTCCGGCTCGTGGCTAAGGGATGTTTG
GGACTGGATATGCACGGTGTTGACTGACTTCAAGACCTGGCTCCAGTCCAAGCTCCTGCCG
```

FIG. 4A

CAGCTACCGGGAGTCCCTTTTTTCTCGTGCCAACGCGGGTACAAGGGAGTCTGGCGGGGAG
ACGGCATCATGCAAACCACCTGCCCATGTGGAGCACAGATCACCGGACATGTCAAAAACGG
TTCCATGAGGATCGTCGGGCCTAAGACCTGCAGCAACACGTGGCATGGAACATTCCCCATC
AACGCATACACCACGGGCCCCTGCACACCCTCTCCAGCGCCAAACTATTCTAGGGCGCTGT
GGCGGGTGGCCGCTGAGGAGTACGTGGAGGTCACGCGGGTGGGGATTTCCACTACGTGAC
GGGCATGACCACTGACAACGTAAAGTGCCCATGCCAGGTTCCGGCTCCTGAATTCTTCACG
GAGGTGGACGGAGTGCGGTTGCACAGGTACGCTCCGGCGTGCAGGCCTCTCCTACGGGAGG
AGGTTACATTCCAGGTCGGGCTCAACCAATACCTGGTTGGGTCACAGCTACCATGCGAGCC
CGAACCGGATGTAGCAGTGCTCACTTCCATGCTCACCGACCCCTCCCACATCACAGCAGAA
ACGGCTAAGCGTAGGTTGGCCAGGGGGTCTCCCCCCTCCTTGGCCAGCTCTTCAGCTATCC
AGTTGTCTGCGCCTTCCTTGAAGGCGACATGCACTACCACCATGTCTCTCCGGACGCTGA
CCTCATCGAGGCCAACCTCCTGTGGCGGCAGGAGATGGGCGGGA$x^1$CATCACCCGCGTGGAG
TCGGAGAACAAGGTGGTAGTCCTGGACTCTTTCGACCCGCTTCGAGCGGAGGAGGATGAGA
GGGAAGTATCCGTTCCGGCGGAGATCCTGCGGAAATCCAAGAAGTTCCCCGCAGCGATGCC
CATCTGGGCGCGCCCGGATTACAACCCTCCACTGTTAGAGTCCTGGAAGGACCCGGACTAC
GTCCCTCCGGTGGTGCACGGGTGCCCGTTGCCACCTATCAAGGCCCCTCCAATACCACCTC
CACGGAGAAAGAGGACGGTTGTCCTAACAGAGTCCTCCGTGTCTTCTGCCTTAGCGGAGCT
CGCTACTAAGACCTTCGGCAGCTCCGAATCATCGGCCGTCGACAGCGGCACGGCGACCGCC
CTTCCTGACCAGGCCTCCGACGACGGTGACAAAGGATCCGACGTTGAGTCGTACTCCTCCA
TGCCCCCCTTGAGGGGGAACCGGGGGACCCCGATCTCAGTGACGGGTCTTGGTCTACCGT
GAGCGAGGAAGCTAGTGAGGATGTCGTCTGCTGC

FIG. 4B

```
GCCTCCAAAGCCGCCCTCATTGAGGAAGGGCAGCGGATGGCGGAGATGCTCAAATCTAAGATACAAGGCCTCCT
ACAACAGGCCACAAGGCAAGCTCAAGACATACAGCCAGCTATACAGTCATCATGGCCCAAGCTTGAACAATTTT
GGGCCAAACACATGTGGAACTTCATCAGTGGTATACAGTACCTAGCAGGACTCTCCACCCTACCGGGAAATCCT
GCAGTAGCATCAATGATGGCTTTTAGCGCCGCGCTGACTAGCCCACTACCCACCAGCACCACCATCCTCTTGAA
CATCATGGGAGGATGGTTGGCCTCTCAGATTGCCCCCCCTGCCGGAGCCACTGGCTTCGTTGTCAGTGGTCTAG
TGGGGGCGGCCGTCGGAAGCATAGGCCTGGGTAAGATACTGGTGGACGTTTTGGCCGGGTACGGCGCAGGCATT
TCAGGGGCCCTCGTAGCTTTTAAGATCATGAGCGGCGAGAAGCCCACGGTAGAAGACGTTGTGAATCTCCTGCC
TGCTATTCTGTCTCCTGGTGCGTTGGTAGTGGGAGTCATCTGTGCAGCAATCCTGCGTCGACACGTGGGTCCGG
GAGAGGGGGCTGTGCAGTGGATGAACCGGCTGATAGCGTTCGCCTCGCGGGGTAATCATGCTTCCCCCACGCAC
TATGTGCCTGAGAGCGACGCCGCAGCGCGTGTTACTCAGATCCTCTCCAGCCTTACCATCACTCAGCTGCTGAA
AAGGCTCCACCAGTGGATTAATGAAGACTGCTCCACACCGTGT
```

FIG. 5A

ASKAALIEEGQRMAEMLKSKIQGLLQQATRQAQDIQPAIQSSWPKLEQFWAKHMWNFISGIQYLAGLSTLPGNP
AVASMMAFSAALTSPLPTSTTILLNIMGGWLASQIAPPAGATGFVVSGLVGAAVGSIGLGKILVDVLAGYGAGI
SGALVAFKIMSGEKPTVEDVVNLLPAILSPGALVVGVICAAILRRHVGPGEGAVQWMNRLIAFASRGNHASPTH
YVPESDAAARVTQILSSLTITQLLKRLHQWINEDCSTPC

FIG. 5B

HCV REPLICONS CONTAINING NS5B FROM GENOTYPE 2B

CROSS-REFERENCE TO RELATED APPLICATIONS

The present application claims the benefit of U.S. Provisional Application No. 60/517,605, filed Nov. 5, 2003, hereby incorporated by reference herein.

BACKGROUND OF THE INVENTION

The references cited in the present application are not admitted to be prior art to the claimed invention.

It is estimated that about 3% of the world's population are infected with the Hepatitis C virus (HCV). (Wasley et al., 2000. *Semin. Liver Dis.* 20, 1-16.) Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) Epidemiological surveys indicate HCV plays an important role in hepatocellular carcinoma pathogenesis. (Kew, 1994. *FEMS Microbiol. Rev.* 14, 211-220, Alter, 1995. *Blood* 85, 1681-1695.)

The HCV genome consists of a single strand RNA about 9.5 kb in length, encoding a precursor polyprotein about 3000 amino acids. (Choo et al., 1989. *Science* 244, 362-364, Choo et al., 1989. *Science* 244, 359-362, Takamizawa et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., 1994. *J. Virol.* 68, 2731-2734, Hijikata et al., 1993. *Proc. Natl. Acad. Sci. USA* 90, 10773-10777.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al., 1993. *J. Virol.* 67, 1385-1395, Hijikata et al., 1993. *Proc. Natl. Acad. Sci. USA* 90, 10773-10777.)

A distinct serine protease located in the N-terminal domain of NS3 is responsible for proteolytic cleavages at the NS3/NS4A, NS4A/NS4B, NS4B/NS5A and NS5A/NS5B junctions. (Barthenschlager et al., 1993. *J. Virol.* 67, 3835-3844, Grakoui et al., 1993. *Proc. Natl. Acad. Sci. USA* 90, 10583-10587, Tomei et al., 1993. *J. Virol.* 67, 4017-4026.) RNA stimulated NTPase and helicase activities are located in the C-terminal domain of NS3.

NS4A provides a cofactor for NS3 protease activity. (Failla et al., *J. Virol.* 1994. 68, 3753-3760, De Francesco et al., U.S. Pat. No. 5,739,002.)

NS5A is a highly phosphorylated protein conferring interferon resistance. (Pawlotsky 1999. *J. Viral Hepat. Suppl.* 1, 47-48.)

NS5B provides an RNA-dependent RNA polymerase. (De Francesco et al., U.S. Pat. No. 6,383,768, Behrens et al., 1996. *EMBO* 15, 12-22, Lohmann et al., 1998. *Virology* 249, 108-118.) Efficient replication in cell culture has been associated with adaptive mutations that dramatically increase the frequency with which replication is established. (Ikeda et al., 2002. *J. Virol.* 76, 2997-3006, Blight et al., 2000. *Science* 290, 1972-1974, Lohman et al., 2001. *J. Virol.* 75, 1437-1449, Kriege et al., 2001. *J. Virol.* 75, 4614-4624.) Adaptive mutations in the HCV-con1 isolate have been localized to various non-structural genes, though substitutions upstream of the interferon sensitivity determining region in NS5A, for example S232I, appears to be the most effective. (Blight et al., 2000. *Science* 290, 1972-1974.) A 4 amino acid insertion in NS5A that is not commonly observed in vivo is important for replication in cell culture of the HCV-N isolate. (Ikeda et al., 2002. *J. Virol.* 76, 2997-3006.) Substitution in residue 470 combined with an NS5A-S232I adaptive mutation were found to be important for conferring cell culture replication to otherwise inactive replicons, including replicons derived from genotype 1b HCV-BK and genotype 1b HCV-H77. (Grobler et al., 2003, *J. of Biological Chemistry* 278:16741-16746.)

SUMMARY OF THE INVENTION

The present invention features methods for enhancing the ability of a genotype 2b NS5B sequence to function in a replicon, for producing replicons containing a functional genotype 2b NS5B, and for using replicons to measure the ability of a compound to affect HCV replication that is sustained with the genotype 2b polymerase. Also featured is a genotype 1b NS4B adaptive mutation. The ability to produce replicons containing a functional genotype 2b NS5B is illustrated by the production of chimeric replicons based on HCV genotype 1b where substantially all the NS5B sequence is replaced with a genotype 2b NS5B.

A HCV replicon is an RNA molecule able to autonomously replicate in a cultured cell, such as Huh7, and produce detectable levels of one or more HCV proteins. The HCV replicon expresses the HCV derived components of the replication machinery and contains cis-elements required for replication in a cultured cell.

Thus, a first aspect of the present invention features a method of enhancing the ability of a genotype 2b NS5B sequence to function in a replicon. The method comprises the step of altering either, or both:

(a) a genotype 2b NS5B sequence to encode one or more adaptive mutations selected from the group consisting of: serine corresponding to position 24 of SEQ ID NO: 1; isoleucine corresponding to position 31 of SEQ ID NO: 1; leucine corresponding to position 392 of SEQ ID NO: 1; or (b) a genotype 2b NS4B to encode an adaptive mutation of alanine corresponding to position 218 of SEQ ID NO: 28.

SEQ ID NO: 1 provides a genotype 2b NS5B sequence providing examples of adaptive mutations. SEQ ID NO: 28 provides a genotype 1 NS4B sequence providing an example of an adaptive mutation. The exact amino acid numbering may vary for different replicon constructs. A "corresponding" position in different constructs can be identified by aligning the relevant regions in the constructs to achieve the greatest degree of homology around the position in question.

Another aspect of the present invention features a method of producing a chimeric replicon having a detectable level of expression. The method comprises the step of replacing substantially all of a NS5B sequence of a HCV replicon comprising a NS3-NS4-NS5A-NS5B ("NS3-5B") genotype 1b sequence with a genotype 2b NS5B encoding nucleic acid sequence.

The NS3-5B sequence itself can be modified to contain adaptive mutations. For example, the NS3-5B sequence may contain a V218A mutation.

Replacing "substantially all" indicates that all or most of a NS5B sequence is replaced and the resulting sequence is a NS5B genotype 2b sequence. Replacement can be achieved by different techniques such as recombinant nucleic acid techniques used to modify a nucleic acid sequence and/or synthesis techniques used to produce a particular sequence.

Another aspect of the present invention describes a chimeric replicon having a detectable level of expression. The chimeric replicon comprises an NS3-NS4-NS5A ("NS3-5A") sequence of a genotype 1b replicon and a genotype 2b NS5B encoding nucleic acid sequence.

Another aspect of the present invention features a recombinant cell. The cell comprises a chimeric replicon containing a NS5B genotype 2b sequence. The replicon replicates in the cell and replicon encoded protein are expressed.

Another aspect of the present invention features a method of measuring the ability of a compound to inhibit replicon activity. The method involves the steps of:

a) providing the compound to a recombinant cell containing a chimeric replicon with a NS5B genotype 2b sequence, and b) measuring the ability of the compound to affect replicon activity.

Unless particular terms are mutually exclusive, reference to "of" indicates either or both possibilities. Occasionally phrases such as "and/or" are used to highlight either or both possibilities.

Reference to "comprises" is open-ended allowing for additional elements or steps. Occasionally phrases such as "one or more" are used with or without "comprises" to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates an amino acid sequence (SEQ ID NO: 1) showing different changes to a NS5B genotype 2b sequence. $Z^1$ is threonine or serine, where threonine was found in a genotype 1b NS5B, and serine was found in a genotype 2b. $X^1$ is asparagine or serine, where serine was identified as an adaptive mutation. $X^2$ is methionine or isoleucine, where isoleucine was identified as an adaptive mutation. $X^3$ is isoleucine or leucine, where leucine is identified as an adaptive mutation. The adaptive mutations N24S, M31I, and I392L individually conferred replication competence in chimera replicon constructs. The underlined sequence represents sequence derived from genotype 1b NS5B that was present in the chimeric construct.

FIG. 2 illustrates a nucleotide sequence encoding the amino acid sequence of SEQ ID NO: 1. The underlined sequence represents sequence derived from a genotype 1b NS5B that was present in the chimeric construct. $X^1$ is A or G, where G creates a serine adaptive mutation at amino acid 24. $X^2$ is G or T, where T creates an isoleucine adaptive mutation at amino acid 31. $X^3$ is A or C, where C creates a leucine adaptive mutation at amino acid 392. $Y^1$ is A found in a genotype 1b NS5B, where T was found in genotype 2b NS5B. $Y^2$ is C found in genotype 1b, where A was found in a genotype 2b NS5B. $Y^3$ is A found in a genotype 1b NS5B, where T was found in a genotype 2b NS5B. $Y^4$ is A found in a genotype 1b NS5B, where C was found in a genotype 2b NS5B. $Y^5$ is A found in a genotype 1b NS5B, where G was found in a genotype 2b NS5B. $Y^6$ is C found in a genotype 1b NS5B, where G was found in a genotype 2b NS5B. $Y^7$ is T found in a genotype 1b NS5B, where C was found in a genotype 2b NS5B. $Y^8$ is G found in a genotype 1b NS5B, where C was found in a genotype 2b NS5B. $Y^9$ is C found in a genotype 1b, where A was found in a genotype 2b NS5B.

FIG. 3 illustrates a NS3-5A amino acid sequence of a genotype 1b (SEQ ID NO: 3). $X^1$ is an adaptive asparagine to serine mutation, and $X^2$ is an adaptive mutation of alanine for valine.

FIGS. 4A and 4B illustrate a nucleotide sequence encoding SEQ ID NO: 3. $X^1$ is A or G, G was found to create Ser adaptive mutation at amino acid 268 of NS5A. $X^2$ is T or C, C was found to create the Ala adaptive mutation at amino acid 218 or NS4B.

FIGS. 5A and 5B illustrates a nucleic acid sequence (SEQ ID NO: 27) for NS4B of genotype 1 containing an adaptive mutation and the encoded polypeptide (SEQ ID NO: 28). The altered codon in FIG. 5A is shown in bold and underlined. The wild-type codon is GTT. The altered amino acid in FIG. 5B is shown in bold and underlined. The wild-type amino acid is valine.

DETAILED DESCRIPTION OF THE INVENTION

HCV replicons provide a cell culture system for measuring the ability of a compound to affect HCV replication. Compounds inhibiting HCV replication have research and therapeutic applications. Therapeutic applications include using those compounds having appropriate pharmacological properties such as efficacy and lack of unacceptable toxicity to treat or inhibit onset of HCV in a patient.

Replicons containing NS5B from genotype 2b can be used by themselves to measure the effect of a compound on HCV activity and can used as part of a panel of different replicons to evaluate the activity of a compound against HCV NS5B present in different HCV isolates. For example, a compound targeting NS5B can be tested using a first replicon containing NS3-NS5B of genotype 1b and second replicon produced from the first replicon where at least substantially all the genotype 1b NS5B sequence is replaced with a NS5B genotype 2b sequence.

The identification of genotype 2b NS5B adaptive mutations facilitates the use of different genotype 2b NS5B sequences, including sequences obtained from clinical isolates. Replicons containing the NS5B sequences obtained from clinical isolates can be used to evaluate the effectiveness of a compound against different HCV isolates and provide an indication of the effectiveness of a compound in a particular individual.

I. Genotype 2b NS5B Sequence

Genotype 2b NS5B sequences described herein contain an amino acid sequence substantially similar to the amino acid sequence of SEQ ID NO: 1, wherein $Z^1$ is serine, $X^1$ is asparagine, $X^2$ is methionine, and $X^3$ is isoleucine ("prototype NS5B genotype 2b sequence"). Genotype 2b NS5B sequences include different naturally occurring sequences and modifications of naturally occurring sequences having a substantially similar sequence as the prototype NS5B genotype 2b sequence.

The prototype NS5B genotype 2b sequence provides a reference point for a genotype 2b NS5B. A sequence substantially similar to the prototype NS5B genotype 2b has a sequence identity of at least 90% to the prototype NS5B genotype 2b sequence. Percent identity is calculated by determining the number of amino acids within the test sequence that are identical to the reference sequence, dividing this number by the total number of residues, then multiplying this fraction by 100. Amino acid alterations can be any combination of additions, deletions, or substitutions.

FIG. 1 illustrates an amino acid sequence providing some examples of different amino acids of a NS5B genotype 2b (SEQ ID NO: 1). The underlined sequence represents a sequence from genotype 1b NS5B. $Z^1$ is threonine in genotype 1b NS5B, serine in genotype 2b NS5B. $X^1$ is asparagine or serine, where serine was identified as an adaptive mutation. $X^2$ is methionine or isoleucine, where isoleucine was identified as an adaptive mutation. $X^3$ is isoleucine or leucine, where leucine is identified as an adaptive mutation.

Preferred genotype 2b NS5B sequences contain one or more of the following adaptive mutations: 24S, 31I and 392L. More preferably, the genotype 2b NS5B sequence has a 31I amino acid.

Adaptive mutations can be introduced into a sequence or it is possible that they may be present in a naturally occurring sequence. The HCV sequence has a high rate of sequence variability and mutation due to the error-prone mechanism of NS5B polymerase, which randomly mis-incorporates ribonucleotides at a rate of approximately $10^{-4}$.

In additional embodiments the genotype 2b NS5B amino acid sequence is provided by SEQ ID NO: 1 wherein either $Z^1$ is threonine or serine, $X^1$ is asparagine or serine, $X^2$ is isoleucine, and $X^3$ is isoleucine or leucine; or $Z^1$ is threonine, $X^1$ is asparagine, $X^2$ is isoleucine, and $X^3$ is isoleucine.

FIG. 2 illustrates a nucleotide sequence (SEQ ID NO: 2) encoding the amino acid sequence of SEQ ID NO: 1. The underlined sequence represents a sequence from a genotype 1b NS5B sequence. $X^1$, $X^2$, $X^3$, $Y^1$, $Y^2$, $Y^3$, $Y^4$, $Y^5$, $Y^6$, $Y^7$, $Y^8$, and $Y^9$ are as described in the Brief Description of the Drawings supra.

Preferred genotype 2b NS5B encoding sequences provide one or more of the following adaptive mutations: 24S, 31S and 392L. These adaptive mutations can be introduced into a sequence or it is possible that they may be present in a naturally occurring sequence. Preferably, the genotype 2b NS5B sequence encodes 31I.

In additional embodiments the genotype 2b NS5B encoding sequence encodes SEQ ID NO: 1 wherein either $Z^1$ is threonine or serine, $X^1$ is asparagine or serine, $X^2$ is isoleucine, and $X^3$ is isoleucine or leucine; or $Y^1$ is threonine, $X^1$ is asparagine, $X^2$ is isoleucine, and $X^3$ is isoleucine.

In additional embodiments the genotype 2b NS5B encoding sequence is provided by SEQ ID NO: 2, wherein $X^1$ is A or G, $X^2$ is T, $X^3$ is A or C, $Y^1$ is A or T, $Y^2$ is C or A, $Y^3$ is A or T, $Y^4$ is A or C, $Y^5$ is A or G, $Y^6$ is C or G, $Y^7$ is T or C; $Y^8$ is G or C, and $Y^9$ is C or A; or $X^1$ is A, $X^2$ is T, V is A, $Y^1$ is A or T, $Y^2$ is C or A, $Y^3$ is A or T, $Y^4$ is A or C, $Y^5$ is A or G, $Y^6$ is C or G, $Y^7$ is T or C; $Y^8$ is G or C, and $Y^9$ is C or A.

Additional genotype 2b NS5B adaptive mutations can be selected using techniques described herein. Examples of such techniques are provided in the Examples infra.

II. Chimeric Replicons

Chimeric replicon providing functional genotype 2b NS5B activity can be produced by combining a NS3-5A genotype 1b encoding sequence of a replicon with a genotype 2b NS5B encoding nucleic acid sequence. The genotype 2b NS5B encoding nucleic acid sequence can be enhanced as described in Section I supra and the Examples infra. The NS3-5A encoding sequence can be modified to contain one or more adaptive mutation.

The basic subunit of an HCV replicon encodes a HCV NS3-NS5B polyprotein along with a suitable 5'-UTR-partial core (PC) region and 3'-UTR. Additional regions may be present including those coding for HCV proteins or elements such as the complete core, E1, E2, p7 or NS2; and those coding for other types of proteins or elements such as an encephalomyocarditis virus (EMCV), internal ribosome entry site (IRES), a reporter protein, or a selection protein.

The HCV 5'-UTR-PC region provides an IRES for protein translation and elements needed for replication. The HCV 5'-UTR-PC region includes naturally occurring HCV 5'-UTR extending about 36 nucleotides into a HCV core encoding region, and functional derivatives thereof. The IRES and PC can be present in different locations such as a site downstream from a sequence encoding a selection protein, a reporter protein, or an HCV polyprotein.

Functional derivatives of the 5'-UTR-PC region able to initiate translation and assist replication can be designed taking into account structural requirements for HCV translation initiation. (See, for example, Honda et al., 1996. *Virology* 222, 31-42.) The effect of different modifications to a 5'-UTR-PC region can be determined using techniques measuring replicon activity.

In addition to the HCV 5'-UTR-PC region, other types of IRES elements can also be present in a replicon. Other types of IRES elements can be present in different locations including immediately upstream of the region encoding an HCV polyprotein. Examples of non-HCV IRES elements that can be used are the EMCV IRES, poliovirus IRES, and bovine viral diarrhea virus IRES.

The HCV 3'-UTR assists HCV replication. HCV 3'-UTR includes naturally occurring HCV 3'-UTR and functional derivatives thereof. Naturally occurring 3'-UTR's have a poly U tract and an additional region of about 100 nucleotides. (Tanaka et al., 1996. *J. Virol.* 70, 3307-3312, Kolykhalov et al., 1996. *J. Virol.* 70, 3363-3371.) At least in vivo, the 3'-UTR appears to be essential for replication. (Kolykhalov et al., 2000. *J. Virol.* 4, 2046-2051.) Examples of naturally occurring 3' UTR derivatives are described by Bartenschlager, U.S. Pat. No. 6,630,343.

The NS3-NS5B polyprotein encoding region provides for a polyprotein that can be processed in a cell into different proteins. Proper processing can be measured by assaying, for example, HCV protein production.

An HCV replicon may contain non-HCV sequences in addition to HCV sequences. The additional sequences should not prevent replication and expression, and preferably serve a useful function. Sequences that can be used to serve a useful function include a selection sequence, a reporter sequence, transcription elements, translation elements and a ribozyme to generate the authentic 3' end of the HCV RNA.

A selection sequence in a HCV replicon facilitates the identification and/or isolation of a cell containing the replicon. Selection sequences providing resistance to an agent that inhibits cell growth can be used in conjunction with selective pressure inhibiting growth of cells not containing the selection sequence. Examples of selection sequences include sequences encoding antibiotic resistance, and ribozymes; and reporters compatible with cell sorting such as green fluorescence protein and beta-lactamase.

Antibiotic resistance can be used in conjunction with an antibiotic to select for cells containing replicons. Examples of selection sequences providing antibiotic resistance are sequences encoding resistance to neomycin, hygromycin, puromycin, or zeocin.

A ribozyme serving as a selection sequence can be used in conjunction with an inhibitory nucleic acid molecule preventing cellular growth. The ribozyme recognizes and cleaves the inhibitory nucleic acid.

A reporter sequence can be used to detect replicon replication or protein expression. Preferred reporter proteins are enzymatic proteins whose presence can be detected by measuring product produced by the protein, or non-enzymatic proteins which can be measured directly. Examples of reporter proteins, both enzymatic and non-enzymatic, include luciferase, beta-lactamase, secretory alkaline phosphatase, beta-glucuronidase, and green fluorescent protein. In addition, a reporter nucleic acid sequence can be used to provide a reference sequence that can be targeted by a complementary nucleic acid probe. Hybridization of the complementary nucleic acid probe to its target can be determined using standard techniques.

Replicons containing reporter sequences may or may not also contain a selection sequence. Selection sequences providing resistance to an agent inhibiting cell growth can be used in conjunction with selective pressure to select for cells maintaining the replicon.

Additional sequences can be part of the same cistron as the HCV polyprotein or can be a separate cistron. If part of the same cistron, additional sequences coding for a protein should result in a product that is either active as a chimeric protein or is cleaved inside a cell so it is separated from HCV protein.

Selection and reporter sequences encoding a protein when present as a separate cistron should be associated with elements needed for translation. Such elements include an IRES 5' to the selection or reporter sequence.

A preferred construct is a bicistronic replicon, where one cistron encodes a selection or reporter sequence and the second cistron encodes HCV proteins. More preferably, the first cistron contains a HCV 5'-UTR-PC region joined to the selection or reporter sequence; and the second cistron contains the EMCV internal ribosome entry site, NS2-NS5B or NS3-NS5B, and a 3'-UTR.

The production and use of replicons containing HCV genotype 1b NS3-5B sequences with adaptive mutations are well known in art. (See, for example, Lohmann et al., *Science* 285, 110-113, 1999, Blight et al., *Science* 290, 1972-1974, 2000, Lohmann et al., *Journal of Virology* 75, 1437-1449, 2001, Pietschmann et al., *Journal of Virology* 75, 1252-1264, 2001, Krieger et al., *J. of Virology* 75: 4614-4624, 2001, Bartenschlager, *Nat. Rev. Drug Discov.* 1(11): 911-916, 2002, Carroll et al., *J. Biological Chemistry,* 278: 11979-11984, 2003, Grobler et al., *J. of Biological Chemistry* 278:16741-16746, 2003, Murray et al., *J. of Virology* 77: 2928-2935, 2003, Vrolijk et al., *J. Virol. Methods* 10(2): 201-209, 2003, Lohmann et al., *J. Virol.* 77(5): 3007-3019, 2003, Bartenschlager, U.S. Pat. No. 6,630,343, Rice et al., International Publication Number WO 01/89364, published Nov. 29, 2001, Bichko International Publication Number WO 02/238793, published May 16, 2002, Kukolj et al., International Publication Number WO 02/052015, published Jul. 4, 2002, De Francesco et al., International Publication Number WO 02/059321, published Aug. 1, 2002.)

SEQ ID NO: 3 provides an example of a genotype 1b NS3-NS5A amino acid sequence from a replicon (FIG. 3). $X^1$ is an adaptive asparagine to serine mutation. $X^2$ is an adaptive valine to alanine mutation.

SEQ ID NO: 4 illustrates a nucleotide sequence encoding SEQ ID NO: 3. (See FIGS. 4A and 4B.)

III. Chimeric Replicon Production

Chimeric replicons can be produced by replacing substantially all of a NS5B sequence of a HCV replicon comprising a NS3-5B genotype 1b sequence with a genotype 2b NS5B encoding nucleic acid sequence. Replacing "substantially all" replaces a sufficient amount of the NS5B sequence such that the resulting sequence is a NS5B genotype 2b sequence. "Substantially all" indicates replacing the entire sequence or a portion of the entire sequence.

Replacement can be achieved by different techniques such as recombinant nucleic acid techniques used to modify a nucleic acid sequence and/or synthesis techniques used to produce a particular sequence. Techniques for altering nucleotides and synthesizing nucleotides are well known in the art. (Ausubel, *Current Protocols in Molecular Biology*, John Wiley, 1987-1998, and Sambrook et al., *Molecular Cloning, A Laboratory Manual*, $2^{nd}$ Edition, Cold Spring Harbor Laboratory Press, 1989.)

Nucleic acid encoding a particular amino acid sequence can be obtained taking into account the genetic code. Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Replicon activity can be measured using techniques such those described in references dealing with adaptive mutations (Section II. supra.), and those described in the Examples infra.

In different embodiments, a chimeric replicon is produced encoding the genotype 1b NS3-NS5A provided by SEQ ID NO: 3, and the genotype 2b NS5B provided by SEQ ID NO: 1 containing one or more adaptive mutation enhancing NS5B activity; and the replicon comprises the genotype 1b NS3-NS5A nucleotide sequence provided by SEQ ID NO: 4 optionally containing one or more adaptive mutations, and the genotype 2b NS5B provided by SEQ ID NO: 2 containing one or more adaptive mutation enhancing NS5B activity. A preferred adaptive mutation is 31I.

IV. Resistance Phenotyping

Resistance phenotyping can be performed to determine the effect of a particular compound on different HCV isolates. Resistance phenotyping can be defined as determining whether a mutation confers resistance to a compound of interest within the genetic background of a circulating variant obtained from a patient sample. The guidance provided herein can be employed to produce replicons containing different genotype 2b NS5B activities. For example, a genotype 2b NS5B can be isolated from a clinical sample, modified to contain a useful adaptive mutation, and then used to replace substantially all the NS5B of a genotype 1b replicon. The ability of a compound to effect chimeric replicon activity can be evaluated. Mutations that were demonstrated in cell culture to confer resistance to this compound can be engineered into this construct, and resistance determined in the genetic context of this variant.

V. Host Cells

Preferred cells for use with a HCV replicon are Huh-7 cells and Huh-7 derived cells. "Huh-7 derived cells" are cells produced starting with Huh-7 cells and introducing one or more phenotypic and/or genotypic modifications.

Huh-7 derived cells include replicon enhanced cells produced from Huh-7. Replicon enhanced cells can be obtained by introducing a replicon into a cell, selecting for cells supporting replicon activity, and completely or partially curing the cells of the replicon. The cured or partially cured cells can be used as a host for introducing another replicon. (De Francesco et al., International Publication Number WO 02/059321, published Aug. 1, 2002, Murray et al., *J. of Virology,* 77:2928-2935, 2003.)

VI. Detection Methods

Methods for detecting replicon activity include those measuring the production or activity of replicon RNA and encoded protein. Measuring can be by qualitative or quantitative analysis. Preferably, replicon activity is measured using a reporter protein.

Preferred reporters are beta-lactamases and luciferases. Beta-lactamases are enzymes catalyzing the cleavage of the beta-lactam ring present in cephalosporins. Different naturally occurring beta-lactamases and functional derivatives of naturally occurring beta-lactamases are well known in the art. (For example, see, Ambler, *Phil. Trans R. Soc. Lond*. Ser. B. 1980. 289, 321-331, Kadonaga et al., 1984. *J. Biol. Chem.* 259, 2149-2154, and U.S. Pat. No. 5,744,320.)

Intracellular beta-lactamase activity is preferably measured using a fluorogenic substrate cleaved by beta-lactamase. Preferred substrates are membrane permeant fluorogenic substrates that become membrane impermeant inside a cell, and that are cleaved by beta-lactamase to produce a detectable signal. Examples of such substrates are provided in Zlokarnik et al., 1998. *Science* 279, 84-88, and Tsien et al., U.S. Pat. No. 5,741,657.

Beta-lactamase activity can be measured, for example, using a cell-permeant fluorescent beta-lactamase substrate such as CCF2-AM or CCF4-AM (Aurora Biosciences, Inc., San Diego, Calif.). These substrates contain an ester group facilitating transport across the cell membrane. Inside the cell, the ester group is cleaved rendering the substrate membrane impermeant. The intact substrates when stimulated with light of ~405 nm, emit green fluorescence (~530 nm) due to resonant energy transfer from a coumarin to fluorescein dye molecule. Cleavage of the substrate by beta-lactamase disrupts the resonance energy transfer and, the fluorescence emission changes to a blue color (~460 nm) of only the coumarin. The fluorescence emissions of the substrate present in the cells can be detected by, for example, fluorescence microscopy or by a fluorometer in conjunction with appropriate emission and excitation filters.

Beta-lactamase inhibitors such as clavulanic acid can be used to enhance a beta-lactamase reporter system by being present throughout the assay. For example, clavulanic acid being present throughout an assay involving an HCV replicon beta-lactamase reporter sensitizes the assay towards HCV replication inhibitors.

Beta-lactamase activity can be measured, for example, by direct visualization of cells using a fluorescence microscope. Quantitation of HCV replication can be accomplished using a CCD camera acquiring digital images and suitable software quantitating the number of blue and green cells present in such images. This method quantitates the number of cells in a population harboring HCV replicons expressing beta-lactamase and this measurement is typically expressed as percentage of blue cells (% Blue cells).

Another method for measuring beta-lactamase activity employs a fluorescence plate reader that quantitates the amount and green (~530 nm) or blue (~460 nm) fluorescence emitted by cells stimulated with light of ~405 nm. This method can be used for high throughput screening.

Quantitation of beta-lactamase activity can also be accomplished by FACS. This method quantitates the number of blue and green cells in a given cell population as well as the amount of blue and green fluorescence. Instruments capable of cell sorting can be used to isolate cells harboring HCV replicons expressing beta-lactamase.

Techniques suitable for measuring RNA production include those detecting the presence or activity of RNA. RNA can be detected using, for example, complementary hybridization probes or quantitative PCR. Techniques for measuring hybridization between complementary nucleic acids and quantitative PCR are well known in the art. (See for example, Ausubel, *Current Protocols in Molecular Biology*, John Wiley, 1987-1998, Sambrook et al., *Molecular Cloning, A Laboratory Manual,* 2nd Edition, Cold Spring Harbor Laboratory Press, 1989, and U.S. Pat. No. 5,731,148.)

RNA enzymatic activity can be provided to the replicon by using a ribozyme sequence. Ribozyme activity can be measured using techniques detecting the ability of the ribozyme to cleave a target sequence.

Techniques measuring protein production include those detecting the presence or activity of a produced protein. The presence of a particular protein can be determined by, for example, immunological techniques. Protein activity can be measured based on the activity of an HCV protein or a reporter protein sequence.

Techniques for measuring HCV protein activity vary depending upon the protein that is measured. Techniques for measuring the activity of different non-structural proteins such as NS2/3, NS3, and NS5B, are well known in the art. (See, for example, references provided in the Background of the Invention.)

Assays measuring replicon activity also include those detecting virion production from a replicon producing a virion; and those detecting a cytopathic effect from a replicon producing proteins exerting such an effect. Cytopathic effects can be detected by assays suitable to measure cell viability.

Assays measuring replicon activity can be used to evaluate the ability of a compound to modulate HCV activities. Such assays can be carried out by providing one or more test compounds to a cell expressing a HCV replicon and measuring the effect of the compound on replicon activity. If a preparation containing more than one compound modulates replicon activity, individual compounds or smaller groups of compounds can be tested to identify replicon active compounds.

VII. EXAMPLES

Examples are provided below further illustrating different features of the present invention. The examples also illustrate useful methodology for practicing the invention. These examples do not limit the claimed invention.

Example 1

Production of Genotype 2b NS5B Sequence

A genotype 2b NS5b sequence was obtained by rescuing NS3-5B genotype 2b sequences from sera and producing a consensus sequence. The consensus sequence was based on the different sequences that were obtained.

Genotype 2b Sequences Rescue

The NS3-5B portion of the genomic RNA of HCV genotype 2b was rescued from infected chimp sera by RT/PCR. Briefly, viral RNA was isolated from 140 µl of sera using Qiagen's Viral RNA kit. Ten microliters of isolated RNA (⅕ of the total yield) was reverse transcribed into cDNA using Stratagene's ProStar kit and dA(34) (SEQ ID NO: 5) as primer. After cDNA synthesis, the RNA was degraded using 1 µl of RNAses H (1 U/µl) and T1 (100 U/µl) (both from Roche), at 37° C. for 20 minutes. The reaction was heat inactivated at 65° C. for 20 minutes prior to PCR.

PCR was performed using 5 µl of the RT reaction and Roche's Expand Long PCR kit. For PCRI, primers 5' ATG-GAGAAGAAGGTCATTGTGTG (SEQ ID NO: 6) and dA(34) (SEQ ID NO: 5) were used as the forward and reverse primers, respectively. A second, nested PCR was then performed with 10 µl of PCRI, forward primer 5' GCTCCCAT-TACTGCCTACACTCA (SEQ ID NO: 7), and reverse primer 5' CCGCTCTACCGAGCGGGGAGT (SEQ ID NO: 8). PCR reactions were conducted in a Biometra T-gradient cycler, cycling conditions 94° C. for 2 minutes, then 15 cycles at 94° C. for 15 seconds, 56° C. for 40 seconds, then 68° C. for 6.5 minutes, followed by 20 cycles of the same, with a 20 second auto extension added onto each cycle.

The rescued NS3-5B DNA fragment was recovered from a 1% agarose TAE gel using Qiagen's gel extraction kit, and was cloned into Novagen's pSTBlue-1 perfectly blunt cloning system. Individual bacterial colonies were propagated for DNA and sequenced using an ABI 3100 DNA sequencer. Sequences were analyzed with Sequencher (Gene Codes Corp.).

NS5B Consensus Sequence

A consensus NS5B sequence was derived from the sequence of five independent NS3-5B clones. The clone with the fewest NS5B changes from the consensus was used as a template to generate the consensus clone through site-directed mutagenesis. The template NS5B encoding sequence was altered to encode for M229T and A558G substitutions.

Site-directed mutagenesis was performed on a vector generated by subcloning a genotype 2b NS5B gene into pJG1062. Subcloning was achieved by generating a PCR product using the NS5B encoding sequence, digesting with Bcl I and Cla I, and subcloning into the BclI-ClaI sites of vector pJG1062. pJG1062 encodes a BamHI-XbaI fragment of con1. (Grobler et al., *J. of Biological Chemistry* 278: 16741-16746, 2003.)

Example 2

Chimeric HCV Replicon Production

Chimeric HCV replicon were produced containing a NS3-5A genotype 1b based a modified BK (Grobler et al., *J. of Biological Chemistry.* 278:16741-16746, 2003) and a NS5B genotype 2b based sequence. Replicon production involved producing a chimeric construct by joining a NS3-5A genotype 1b sequence, a NS5B genotype 2b sequence, and a neomycin resistant sequence; infecting Huh7 cells with the chimeric construct; and selecting for neomycin resistant colonies. Characterization of neomycin resistant colonies identified three different adaptive mutations.

Chimeric Construct Production

A chimeric construct was produced by replacing substantially all of a NS5B sequence of a NS3-5B genotype 1b replicon with the NS5B genotype 2b sequence. The mutated genotype 2b NS5B encoding sequence from Example 1 was subcloned into pJG1185 as a BclI-ClaI fragment. pJG1185 encodes a subgenomic genotype 1b replicon based on HCV BK with adaptive mutations. (Grobler et al., *J. of Biological Chemistry.* 278:16741-16746, 2003).

The resulting chimeric construct replaced the genotype 1b NS5B with the NS5B genotype 2b clone starting at amino acid residue 11 of NS5B. The clone was designated clone "bla-2b". Clone "neo-2b" was produced by replacing the bla-2b β-lactamase gene with a neomycin phosphotransferase (Neo$^r$) encoding gene. Clone con1-2bM31I discussed in Example 4 is similar to bla-2bM31I except that the NS3-5A replicon sequences are Con1b sequences. This was constructed by cloning the genotype 2b NS5B with M31I as a BclI-ClaI fragment into vector pJG1073. pJG1073 encodes a subgenomic genotype 1b replicon with NS3 through NS5A based on HCV con1. (Grobler et al., *J. of Biological Chemistry.* 278:16741-16746, 2003.)

Selection and Characterization of Neo Resistant Colonies

Neo-2b was used as a starting point to select for adaptive mutations. To generate RNA for transfection, plasmids were linearized by digestion of an XbaI site distal to the replicon sequences. RNA was generated using MEGAscript™ (Ambion, Austin, Tex.) and quantitated by UV absorbance.

Huh-7 cells were seeded at a density of 300,000 cells per well in a 6 well cluster plate 16 hours prior to transfection. Transfection was accomplished using Optimem I and DMRIE-C reagents (Invitrogen Life Technologies) as described by Murray et al., *J. of Virology*, 77:2928-2935, 2003, except 2.5 µg of RNA was used per well for transfection of cells. The day after transfection, cells were split into T150 flasks with peel off tops (TKR Biotech) and maintained in Dulbecco's modified Eagle's medium (DMEM) supplemented with 10% fetal bovine serum, nonessential amino acids, 2 mM GlutaMAX, and Penn/Strep (Invitrogen Corp., Carlsbad, Calif.) containing 250 µg/ml Geneticin (Invitrogen) and a 1/500 dilution (v/v) of Fungizone (Invitrogen). Cells were kept sub-confluent over the course of the selection by expanding into fresh media until neo resistant colonies arose.

Three colonies were obtained and further characterized. The colonies were trypsinized in cloning cylinders (Sigma), then expanded ultimately to T225 flasks. Twenty percent of a T225 harvest ($\sim$1-2$\times$10$^6$ cells) was used in RT/PCR analysis. RNA was isolated from the resistant cell lines using Qiagen's RNA Easy kit. Ten micrograms of isolated RNA was taken for RT using the dA(34) (SEQ ID NO: 5) primer as described above. The RT reaction was treated with RNAses as described earlier, and 5 µl was used for PCR using Novagen's KOD hot start polymerase. Five overlapping, nested, PCR rescues (designated A-E) were performed to recover the NS3-5B region. PCR primers for the fragments were as follows:

```
A:
forward
                                              (SEQ ID NO: 9)
5' CTCTCCTCAAGCGTATTCAACAAGG reverse
                                              SEQ ID NO: 10)
```

```
                                           -continued
5' CCGTGCAGCGTAGGTTTCAGCCGTA forward
                                              (SEQ ID NO: 11)
5' CCCATTGTATGGGATCTGATCTGG reverse
                                              SEQ ID NO: 12)
5' CAAGCTGAAGTCGACTGTCTGGGTGACA B:
forward
                                              (SEQ ID NO: 13)
5' TACTTGGTCACGAGACATGCTGACGTCAT reverse
                                              (SEQ ID NO: 14)
5' GGAGAGGATAGCAGGGAGT forward
                                              (SEQ ID NO: 15)
5' CGTATATGTCTAAGGCACACGGTATTGAC reverse
                                              (SEQ ID NO: 16)
5' GGCTGGTGATAGAGGCTGTGAATGCCAT C:
forward
                                              (SEQ ID NO: 17)
5' GGATCAAATGTGGAAGTGTCTCATACGG reverse
                                              (SEQ ID NO: 18)
5' TCGAGGTTGTGGAGTACAC forward
                                              (SEQ ID NO: 19)
5' GCAATAGCATCATTGATGGCATTCACAGC reverse
                                              (SEQ ID NO: 20)
5' GGCCTCGATGAGGTCAGCGT D:
                                              (SEQ ID NO: 21)
5' CTCTCCTCAAGCGTATTCAACAAGG (SEQ ID NO: 5)
5' d(A34)

(SEQ ID NO: 22)
5' GTAAAGTGCCCGTGTCAGGT reverse
                                              (SEQ ID NO: 23)
5' CATGATAGTTGTGTCAATTGG E:
                                              (SEQ ID NO: 24)
5' GTCTACCGTGAGCGAGGAA (SEQ ID NO: 5)
5' d(A34) reverse (SEQ ID NO: 25)
5' ATACTCCTGGACAGGGCCCT (SEQ ID NO: 26)
5' GCGCGCGCATCGATCGGGAGTAAAAAGATGCCTAC
```

For every set of reactions, the PCR I primers are the first pair in each set, while the PCRII primers are the second. For PCRII, 5 μl of the PCRI reaction was used. Generally, the cycling conditions for PCR were 94° C. 2 minutes, then 94° C. for 15 seconds, 55° C. for 40 seconds, and 68° C. for 2.5 minutes, for 35 cycles.

The PCRII fragments were size fractionated on 1% agarose TAE gels and isolated using Qiagen's gel extraction kit. The fragments were sequenced directly on an ABI 3100 sequencer and analyzed with Sequencher.

Each of the three different surviving cells were found to contain an adaptive mutation conferring replication competence in a chimera construct. The adaptive mutations were N24S, M31I, and I392L in the prototype NS5B 2b sequence.

Example 3

Establishment of Persistently Replicating Cell Lines and Addition of Test Compounds Selection of persistently replication cells lines expressing β-lactamase, using bla:2b chimeric replicons each harboring a different mutation (N24S, M31I, I392L) defined in the Neo$^r$ selection studies described above, was performed in the enhanced replication Huh7 derived cell line MR2. (Murray et al., *J. of Virology*, 77:2928-2935, 2003.) To generate RNA for transfection, plasmids were linearized by digestion of an XbaI site distal to the replicon sequences. RNA was generated using MEGAscript™ (Ambion, Austin, Tex.) and quantitated by UV absorbance.

MR2 was maintained in Dulbecco's modified Eagle's medium (DMEM) supplemented with 10% fetal bovine serum, nonessential amino acids, 2 mM GlutaMAX, and Penn/Strep (Invitrogen Corp., Carlsbad, Calif.). Cells were seeded the night prior to transfection at a density of 300,000 cells per well in a 6-well dish. A mixture of 5 μg RNA, 12 μl of DMRE-C (Invitrogen Corp., Carlsbad, Calif.), and 2 ml of Opti-Mem (Invitrogen Corp., Carlsbad, Calif.) media was prepared and allowed to sit for 10 minutes. During this time media was removed from the MR2 cells, cells were washed once with Opti-Mem, then the RNA:DMRE-C mixture was added dropwise, and incubated for ~8 hours. Transfection media was removed by aspiration, and replaced with 2 ml DMEM. Transfected cells continued to grow overnight.

The next morning cells were expanded into two T75 flasks and grown for an additional three days. A duplicate well for each replicon construct was analyzed for β-lactamase activity to verify that the transfection efficiency was >90%.

On day 4 cells from one flask were collected, counted, and seeded into a 96 well Cytostar plate at a density of 7,500 cells/well in the presence of 1 μM clavulonic acid. The appropriate dilution of an NS5B inhibitor was added immediately in an equal volume, thus adjusting the final clavulonic acid concentration to 0.5 μM. Simultaneously, the other flasks were analyzed for β-lactamase activity to verify both that activity from a non-replicating control sub-genomic replicon was undetectable, and establish the day 4 replication activity of the test replicons. The non-replicating control, con1:GAA, is non-functional due to an Asp-to-Ala substitution of NS5B (wild-type is GDD). Cells with drug were incubated for two days, and analyzed as described in Example 4.

Example 4

Analysis of β-Lactamase Activity

Medium was removed by aspiration and cells were stained for 2 hours with CCF4-AM (Invitrogen Corp., Carlsbad, Calif.) in DMEM supplemented with 25 mM HEPES, pH 8.0. Fluorescence due to β-lactamase activity was measured through excitation at 405 nm, followed by measurement of the emission at 460 nm using a CytoFluor 4000 fluorescence plate reader. Equal cell count and viability was verified by measuring the emission at 530 nm. A tolerance limit of 30% per data set was accepted.

EC$_{50}$ determinations for 2'C-methyladenosine were calculated as a percent of the DMSO control by fitting the data to a 4 parameter fit function using Kaleidagraph software (Synergy Software, Reading, Pa.). The results are shown in Table 1.

TABLE 1

|  | Con1-2bM31I | BK-2bM31I |
|---|---|---|
| EC50 | 407 nM | 667 nM |
| Slope | 1.3 | 1.9 |

"Con1" indicates NS3-NS5A and the first 11 amino acids of modified Con1b described by Lohmann et al., Science 285, 110-113, 1999.
"BK" indicates NS3-NS5A and the first 11 amino acids of modified BK described by Grobler et al., J. of Biological Chemistry. 278: 16741-16746, 2003.
"2bM31I" indicates an adaptive mutation made to the prototype NS5B genotype 2b sequence.

Two bk:2B bla chimeric replicons bearing changes at residues 24 and 392 were not robust enough by themselves for IC$_{50}$ determination, although limited replication which could be inhibited at the EC$_{95}$ for 2'C-methyladenosine could be demonstrated. The combination of these mutations enhanced replication to a level sufficient for drug titration when present in the same construct. In addition, 24S within NS5B, when coupled with a serine at residue 268 of NS5A (within the BK replicon) also supported drug-titratable replication. (See Table 2.)

TABLE 2

|  | EC50 | Slope |
|---|---|---|
| Con1-2bM31I | 407 nM | 1.3 |
| BK-2bM31I | 667 nM | 1.9 |
| BK NS5a268S-2bN24S | 982 nM | 0.81 |
| BK-2b N24S/L392I | 185 nM | 0.56 |

"Con1" "BK" and "2bM31I" are as described in Table 1.
"NS5a268S" indicates an adaptive mutation to "BK" resulting in a serine at position 268 of NS5A.
"2bN24S" indicates an adaptive mutation made to the prototype NS5B genotype 2b sequence.
"N24S/L392I" indicates adaptive mutations made to the prototype NS5B genotype 2b sequence There was no titratable inhibition by compound A in an 8 point titration (3 fold dilutions) from 20 μM to 9 nM (~10% inhibition for both the "Con1" and "BK" versions at 20 μM) for any of the BK:2B or con1:2B constructs described above. Compound A inhibited replication of genotype 1B replicons at sub-micromolar levels. Compound A has the following structure:

An additional G418 resistant cell line from a similar screen with BK:2B RNA was isolated and shown to encode only a single substitution within NS4B, changing the valine at residue 218 to alanine. Chimeric replicons with genotype 2a or 2b NS5B into the NS4B substituted BK replicon (designated BK:4B) showed increased replication fitness.

TABLE 3

| Replicon | Replication Fitness* |
|---|---|
| BK | 1 |
| BK:4B:2b | 0.129 |
| BK:4B:2a.4 | 0.153 |

*normalized to BK
"BK:4B:2a" refers to NS3-5A from strain BK, NS4B having an adaptive mutation (SEQ ID NOs: 27 and 28), and NS5B based on genotypes 2B NS5B sequence (first 10 residues from BK).
"BK:4B:2b.4" refers to NS3-5A from strain BK, NS4B having an adaptive mutation (SEQ ID NOs: 27 and 28), and NS5B based on a genotype 2A sequence first ten residues from BK).

Other embodiments are within the following claims. While several embodiments have been shown and described, various modifications may be made without departing from the spirit and scope of the present invention.

What is claimed is:

1. A method of enhancing the ability of a genotype 2b NS5B sequence to function in a replicon comprising the step of altering either, or both
    (a) said genotype 2b NS5B sequence to encode one or more adaptive mutations selected from the group consisting of:
    serine corresponding to position 24 of SEQ ID NO: 1;
    isoleucine corresponding to position 31 of SEQ ID NO: 1;
    leucine corresponding to position 392 of SEQ ID NO: 1; or
    (b) a genotype 1b NS4B sequence to encode an adaptive mutation of alanine corresponding to position 218 of SEQ ID NO:28.

2. The method of claim 1, wherein altering said genotype 2b NS5B sequence comprises at least isoleucine corresponding to position 31 of SEQ ID NO: 1, or at least serine corresponding to position 24 of SEQ ID NO: 1 in combination with leucine corresponding to position 392 of SEQ ID NO: 1.

3. The method of claim 2, wherein said genotype 2b NS5B sequence is obtained from a clinical isolate.

4. A method of producing a chimeric replicon comprising the step of replacing substantially all of a NS5B sequence of a HCV replicon comprising a NS3-5B genotype 1b sequence encoding SEQ ID NO: 3 with a genotype 2b NS5B encoding nucleic acid sequence.

5. The method of claim 4, further comprising the step of enhancing the ability of said genotype 2b NS5B according to the method of claim 1, wherein said enhancing can be done prior to, or after, said replacing step.

6. The method of claim 5, wherein said genotype 2b NS5B sequence is obtained from a clinical isolate.

7. A chimeric HCV replicon comprising:
    a) a NS3-5A sequence of a genotype 1b replicon or a modified NS3-5A sequence of genotype 1b replicon wherein NS4B contains a V218A modification; and
    b) substantially all of a genotype 2b NS5B encoding nucleic acid sequence.

8. The chimeric replicon of claim 7, further comprising a reporter or selection sequence.

9. The chimeric replicon of claim 7, wherein said genotype 2b NS5B sequence encodes at least one of the following amino acids in the indicated position:

serine corresponding to position 24 of SEQ ID NO: 1;
isoleucine corresponding to position 31 of SEQ ID NO: 1;
leucine corresponding to position 392 of SEQ ID NO: 1.

10. The chimeric replicon of claim 9, wherein said genotype 2b NS5B sequence encodes at least isoleucine corresponding to position 31 of SEQ ID NO: 1, or at least serine corresponding to position 24 of SEQ ID NO: 1 in combination with leucine corresponding to position 392 of SEQ ID NO: 1.

11. The chimeric replicon of claim 8, wherein said genotype 2b NS5B sequence encodes NS5B provided by SEQ ID NO: 1.

12. The chimeric replicon of claim 9, wherein said NS3-5A sequence consists of SEQ ID NO: 4 and NS5B sequence consists of SEQ ID NO: 2.

13. The chimeric replicon of claim 12, wherein nucleotide 2711 of SEQ ID NO: 4 is C.

14. A recombinant cell comprising a replicon made the method of claim 1, wherein said replicon is expressed in said cell.

15. A method of measuring the ability of a compound to inhibit replicon activity comprising the steps of:
    a) providing said compound to the recombinant cell of claim 12, and
    b) measuring the ability of said compound to affect replicon activity.

16. A recombinant cell comprising a replicon made by the method of claim 2, wherein said replicon is expressed in said cell.

17. A recombinant cell comprising a replicon made by the method of claim 4, wherein said replicon is expressed in said cell.

18. A recombinant cell comprising the replicon of claim 7, wherein said replicon is expressed in said cell.

19. A recombinant cell comprising the replicon of claim 8, wherein said replicon is expressed in said cell.

20. A recombinant cell comprising the replicon of claim 9, wherein said replicon is expressed in said cell.

* * * * *

SEQUENCE LISTING

```
<160> NUMBER OF SEQ ID NOS: 28

<210> SEQ ID NO 1
<211> LENGTH: 591
<212> TYPE: PRT
<213> ORGANISM: Artificial Sequence
<220> FEATURE:
<223> OTHER INFORMATION: HCV
<221> NAME/KEY: VARIANT
<222> LOCATION: (5)...(5)
<223> OTHER INFORMATION: Xaa = threonine or serine
<221> NAME/KEY: VARIANT
<222> LOCATION: (24)...(24)
<223> OTHER INFORMATION: Xaa = asparagine or serine
<221> NAME/KEY: VARIANT
<222> LOCATION: (31)...(31)
<223> OTHER INFORMATION: Xaa = methionine or isoleucine
<221> NAME/KEY: VARIANT
<222> LOCATION: (392)...(392)
<223> OTHER INFORMATION: Xaa = isoleucine or leucine

<400> SEQUENCE: 1

Ser Met Ser Tyr Xaa Trp Thr Gly Ala Leu Ile Thr Pro Cys Gly Pro
1               5                   10                  15
```

```
Glu Glu Glu Lys Leu Pro Ile Xaa Pro Leu Ser Asn Ser Leu Xaa Arg
                20              25              30

Phe His Asn Lys Val Tyr Ser Thr Thr Ser Arg Ser Ala Ser Leu Arg
        35              40              45

Ala Lys Lys Val Thr Phe Asp Arg Val Gln Val Leu Asp Ala His Tyr
50              55              60

Asp Ser Val Leu Gln Asp Val Lys Arg Ala Ala Ser Lys Val Ser Ala
65              70              75              80

Arg Leu Leu Thr Val Glu Glu Ala Cys Ala Leu Thr Pro His Ser
                85              90              95

Ala Lys Ser Arg Tyr Gly Phe Gly Ala Lys Glu Val Arg Ser Leu Ser
            100             105             110

Arg Arg Ala Val Asn His Ile Arg Ser Val Trp Glu Asp Leu Leu Glu
            115             120             125

Asp Gln His Thr Pro Ile Asp Thr Thr Ile Met Ala Lys Asn Glu Val
    130             135             140

Phe Cys Ile Asp Pro Thr Lys Gly Lys Lys Pro Ala Arg Leu Ile
145             150             155             160

Val Tyr Pro Asp Leu Gly Val Arg Val Cys Glu Lys Met Ala Leu Tyr
                165             170             175

Asp Ile Ala Gln Lys Leu Pro Lys Ala Ile Met Gly Pro Ser Tyr Gly
            180             185             190

Phe Gln Tyr Ser Pro Ala Glu Arg Val Asp Phe Leu Leu Lys Ala Trp
        195             200             205

Gly Ser Lys Lys Asp Pro Met Gly Phe Ser Tyr Asp Thr Arg Cys Phe
            210             215             220

Asp Ser Thr Val Thr Glu Arg Asp Ile Arg Thr Glu Glu Ser Ile Tyr
225             230             235             240

Gln Ala Cys Ser Leu Pro Gln Glu Ala Arg Thr Val Ile His Ser Leu
            245             250             255

Thr Glu Arg Leu Tyr Val Gly Gly Pro Met Thr Asn Ser Lys Gly Gln
        260             265             270

Ser Cys Gly Tyr Arg Arg Cys Arg Ala Ser Gly Val Phe Thr Thr Ser
            275             280             285

Met Gly Asn Thr Met Thr Cys Tyr Ile Lys Ala Leu Ala Ala Cys Lys
        290             295             300

Ala Ala Gly Ile Val Asp Pro Val Met Leu Val Cys Gly Asp Asp Leu
305             310             315             320

Val Val Ile Ser Glu Ser Gln Gly Asn Glu Glu Asp Glu Arg Asn Leu
            325             330             335

Arg Ala Phe Thr Glu Ala Met Thr Arg Tyr Ser Ala Pro Pro Gly Asp
        340             345             350

Leu Pro Arg Pro Glu Tyr Asp Leu Glu Leu Ile Thr Ser Cys Ser Ser
        355             360             365

Asn Val Ser Val Ala Leu Asp Ser Arg Gly Arg Arg Tyr Phe Leu
        370             375             380

Thr Arg Asp Pro Thr Thr Pro Xaa Thr Arg Ala Ala Trp Glu Thr Val
385             390             395             400

Arg His Ser Pro Val Asn Ser Trp Leu Gly Asn Ile Ile Gln Tyr Ala
            405             410             415

Pro Thr Ile Trp Val Arg Met Val Ile Met Thr His Phe Phe Ser Ile
            420             425             430

Leu Leu Ala Gln Asp Thr Leu Asn Gln Asn Leu Asn Phe Glu Met Tyr
```

-continued

```
              435                 440                 445
Gly Ala Val Tyr Ser Val Asn Pro Leu Asp Leu Pro Ala Ile Ile Glu
    450                 455                 460

Arg Leu His Gly Leu Glu Ala Phe Ser Leu His Thr Tyr Ser Pro His
465                 470                 475                 480

Glu Leu Ser Arg Val Ala Ala Thr Leu Arg Lys Leu Gly Ala Pro Pro
                485                 490                 495

Leu Arg Ala Trp Lys Ser Arg Ala Arg Ala Val Arg Ala Ser Leu Ile
            500                 505                 510

Ala Gln Gly Ala Arg Ala Ala Ile Cys Gly Arg Tyr Leu Phe Asn Trp
        515                 520                 525

Ala Val Lys Thr Lys Leu Lys Leu Thr Pro Leu Pro Glu Ala Ser Arg
    530                 535                 540

Leu Asp Leu Ser Gly Trp Phe Thr Val Gly Ala Gly Gly Gly Asp Ile
545                 550                 555                 560

Tyr His Ser Val Ser His Ala Arg Pro Arg Leu Leu Leu Leu Cys Leu
                565                 570                 575

Leu Leu Leu Ser Val Gly Val Gly Ile Phe Leu Leu Pro Asp Arg
            580                 585                 590

<210> SEQ ID NO 2
<211> LENGTH: 1776
<212> TYPE: DNA
<213> ORGANISM: Artificial Sequence
<220> FEATURE:
<223> OTHER INFORMATION: HCV
<221> NAME/KEY: variation
<222> LOCATION: (3)...(3)
<223> OTHER INFORMATION: n = A or T
<221> NAME/KEY: variation
<222> LOCATION: (9)...(9)
<223> OTHER INFORMATION: n = C or A
<221> NAME/KEY: variation
<222> LOCATION: (13)...(13)
<223> OTHER INFORMATION: n = A or T
<221> NAME/KEY: variation
<222> LOCATION: (15)...(15)
<223> OTHER INFORMATION: n = A or C
<221> NAME/KEY: variation
<222> LOCATION: (21)...(21)
<223> OTHER INFORMATION: n - A or G
<221> NAME/KEY: variation
<222> LOCATION: (24)...(24)
<223> OTHER INFORMATION: n = C or G
<221> NAME/KEY: variation
<222> LOCATION: (28)...(28)
<223> OTHER INFORMATION: n = T  or C
<221> NAME/KEY: modified_base
<222> LOCATION: (30)...(30)
<223> OTHER INFORMATION: n = G or C
<221> NAME/KEY: variation
<222> LOCATION: (33)...(33)
<223> OTHER INFORMATION: n = C or A
<221> NAME/KEY: variation
<222> LOCATION: (71)...(71)
<223> OTHER INFORMATION: n = A or G
<221> NAME/KEY: variation
<222> LOCATION: (93)...(93)
<223> OTHER INFORMATION: n = G or T
<221> NAME/KEY: variation
<222> LOCATION: (1174)...(1174)
<223> OTHER INFORMATION: n = A or C

<400> SEQUENCE: 2
tcnatgtcnt acncntggac nggngccntn atnacaccat gtgggcccga agaggagaag      60
ttaccgatca ncccctctgag taattcgctc atncggttcc ataataaggt gtactccaca    120
acctcgagga gtgcctctct gagggcaaag aaggtgactt tgacagggt gcaggtgctg      180
```

-continued

```
gacgcacact atgactcagt cttgcaggac gttaagcggg ccgcctctaa ggttagtgcg    240
aggctcctca cggtagagga agcctgcgcg ctgaccccgc cccactccgc caaatcgcga    300
tacggatttg gggcaaaaga ggtgcgcagc ttatctagga gggccgttaa ccacatccgg    360
tccgtgtggg aggacctcct ggaagaccaa catacccccaa ttgacacaac tatcatggct   420
aaaaatgagg tgttctgcat tgatccaact aaaggtggga aaaagccagc tcgcctcatc    480 gtatacccccg accttggggt cagggtgtgc gaaaagatgg ccctctatga catcgcacaa   540
aagcttccca aagcgataat ggggccatcc tatgggttcc aatactctcc cgcagaacgg    600
gtcgatttcc tcctcaaagc ttggggaagt aagaaggacc caatgggggtt ctcgtatgac   660 acccgctgct ttgactcaac cgtcacggag agggacataa gaacagaaga atccatatat    720
caggcttgtt ctctgcctca agaagccaga actgtcatac actcgctcac tgagagactt    780
tacgtaggag ggcccatgac aaacagcaaa gggcaatcct gcggctacag gcgttgccgc    840
gcaagcggtg ttttcaccac cagcatgggg aataccatga catgttacat caaagcccttt   900 gcagcgtgta aggctgcagg gatcgtggac cctgttatgt tggtgtgtgg agacgacctg    960
gtcgtcatct cagagagcca aggtaacgag gaggacgagc gaaacctgag agcttttcacg  1020 gaggctatga ccaggtattc cgcccctccc ggtgaccttc ccagaccgga atatgacttg   1080
gagcttataa catcctgctc ctcaaacgta tcggtagcgc tggactctcg gggtcgccgc   1140
cggtacttcc taaccagaga ccctaccact ccantcaccc gagctgcttg ggaaacagta   1200
agacactccc ctgtcaattc ttggctgggc aacatcatcc agtacgcccc cacaatctgg   1260
gtccggatgg tcataatgac tcacttcttc tccatactat tggcccagga cactctgaac   1320
caaaatctca attttgagat gtacggggca gtatactcgg tcaatccatt agacctaccg   1380
gccataattg aaaggctaca tgggcttgaa gccttttcac tgcacacata ctctccccac   1440
gaactctcac gggtggcagc aactctcaga aaacttggag cgcctcccct tagagcgtgg   1500
aagagtcggg cgcgtgccgt gagagcttca ctcatcgccc aaggagcgag ggcggccatt   1560
tgtggccgct acctcttcaa ctgggcggtg aaaacaaagc tcaaactcac tccattgccc   1620
gaggcgagcc gcctggattt atccgggtgg ttcaccgtgg gcgccggcgg gggcgacatt   1680
tatcacagcg tgtcgcatgc ccgaccccgc ctattactcc tttgcctact cctacttagc   1740
gtaggagtag gcatcttttt actccccgat cgatga                             1776
```

<210> SEQ ID NO 3
<211> LENGTH: 1394
<212> TYPE: PRT
<213> ORGANISM: Artificial Sequence
<220> FEATURE:
<223> OTHER INFORMATION: HCV
<221> NAME/KEY: VARIANT
<222> LOCATION: (1215)...(1215)
<223> OTHER INFORMATION: Xaa = asparagine or serine
<221> NAME/KEY: VARIANT
<222> LOCATION: (904)...(904)
<223> OTHER INFORMATION: Xaa = valine or alanine

<400> SEQUENCE: 3

```
Met Ala Pro Ile Thr Ala Tyr Ser Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Val Val Ser Thr Ala Thr Gln Ser Phe Leu Ala Thr Cys
         35                  40                  45
```

-continued

```
Val Asn Gly Val Cys Trp Thr Val Tyr His Gly Ala Gly Ser Lys Thr
 50                  55                  60

Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                     85                  90                  95

Pro Cys Thr Cys Gly Ser Ser Asp Leu Tyr Leu Val Thr Arg His Ala
                100                 105                 110

Asp Val Ile Pro Val Arg Arg Arg Gly Asp Ser Arg Gly Ser Leu Leu
            115                 120                 125

Ser Pro Arg Pro Val Ser Tyr Leu Lys Gly Ser Ser Gly Gly Pro Leu
130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350

Lys Ala Ile Pro Ile Glu Ala Ile Arg Gly Gly Arg His Leu Ile Phe
        355                 360                 365

Cys His Ser Lys Lys Lys Cys Asp Glu Leu Ala Ala Lys Leu Ser Gly
370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
450                 455                 460

Arg Thr Gly Arg Gly Arg Met Gly Ile Tyr Arg Phe Val Thr Pro Gly
465                 470                 475                 480
```

```
Glu Arg Pro Ser Gly Met Phe Asp Ser Val Leu Cys Cys Tyr
            485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
            515                 520                 525

His Leu Glu Phe Trp Glu Ser Val Phe Thr Gly Leu Thr His Ile Asp
            530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Leu Thr His Pro Ile Thr Lys Tyr Ile Met Ala Cys Met
        610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Arg Pro Ala Ile Val Pro Asp
            660                 665                 670

Arg Glu Phe Leu Tyr Gln Glu Phe Asp Glu Met Glu Glu Cys Ala Ser
        675                 680                 685

His Leu Pro Tyr Ile Glu Gln Gly Met Gln Leu Ala Glu Gln Phe Lys
        690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765

Thr Ala Ser Ile Thr Ser Pro Leu Thr Thr Gln Ser Thr Leu Leu Phe
        770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
        835                 840                 845

Pro Ser Thr Glu Asp Leu Val Asn Leu Leu Pro Ala Ile Leu Ser Pro
850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Xaa Ser Pro Thr His Tyr Val Pro Glu
```

```
                    900             905             910
Ser Asp Ala Ala Ala Arg Val Thr Gln Ile Leu Ser Ser Leu Thr Ile
                915                 920                 925

Thr Gln Leu Leu Lys Arg Leu His Gln Trp Ile Asn Glu Asp Cys Ser
            930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
                965                 970                 975

Gln Leu Pro Gly Val Pro Phe Phe Ser Cys Gln Arg Gly Tyr Lys Gly
            980                 985                 990

Val Trp Arg Gly Asp Gly Ile Met Gln Thr Thr Cys Pro Cys Gly Ala
        995                 1000                1005

Gln Ile Thr Gly His Val Lys Asn Gly Ser Met Arg Ile Val Gly Pro
    1010                1015                1020

Lys Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
                1045                1050                1055

Leu Trp Arg Val Ala Ala Glu Glu Tyr Val Glu Val Thr Arg Val Gly
            1060                1065                1070

Asp Phe His Tyr Val Thr Gly Met Thr Thr Asp Asn Val Lys Cys Pro
            1075                1080                1085

Cys Gln Val Pro Ala Pro Glu Phe Phe Thr Glu Val Asp Gly Val Arg
        1090                1095                1100

Leu His Arg Tyr Ala Pro Ala Cys Arg Pro Leu Leu Arg Glu Glu Val
1105                1110                1115                1120

Thr Phe Gln Val Gly Leu Asn Gln Tyr Leu Val Gly Ser Gln Leu Pro
                1125                1130                1135

Cys Glu Pro Glu Pro Asp Val Ala Val Leu Thr Ser Met Leu Thr Asp
            1140                1145                1150

Pro Ser His Ile Thr Ala Glu Thr Ala Lys Arg Arg Leu Ala Arg Gly
            1155                1160                1165

Ser Pro Pro Ser Leu Ala Ser Ser Ser Ala Ile Gln Leu Ser Ala Pro
1170                1175                1180

Ser Leu Lys Ala Thr Cys Thr Thr His His Val Ser Pro Asp Ala Asp
1185                1190                1195                1200

Leu Ile Glu Ala Asn Leu Leu Trp Arg Gln Glu Met Gly Gly Xaa Ile
            1205                1210                1215

Thr Arg Val Glu Ser Glu Asn Lys Val Val Val Leu Asp Ser Phe Asp
            1220                1225                1230

Pro Leu Arg Ala Glu Glu Asp Glu Arg Glu Val Ser Val Pro Ala Glu
            1235                1240                1245

Ile Leu Arg Lys Ser Lys Lys Phe Pro Ala Ala Met Pro Ile Trp Ala
            1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ile Lys Ala
                1285                1290                1295

Pro Pro Ile Pro Pro Pro Arg Arg Lys Arg Thr Val Val Leu Thr Glu
            1300                1305                1310

Ser Ser Val Ser Ser Ala Leu Ala Glu Leu Ala Thr Lys Thr Phe Gly
            1315                1320                1325
```

-continued

```
Ser Ser Glu Ser Ser Ala Val Asp Ser Gly Thr Ala Thr Ala Leu Pro
    1330                1335                1340

Asp Gln Ala Ser Asp Asp Gly Asp Lys Gly Ser Asp Val Glu Ser Tyr
1345                1350                1355                1360

Ser Ser Met Pro Pro Leu Glu Gly Glu Pro Gly Asp Pro Asp Leu Ser
            1365                1370                1375

Asp Gly Ser Trp Ser Thr Val Ser Glu Glu Ala Ser Glu Asp Val Val
        1380                1385                1390

Cys Cys

<210> SEQ ID NO 4
<211> LENGTH: 4182
<212> TYPE: DNA
<213> ORGANISM: Artificial Sequence
<220> FEATURE:
<223> OTHER INFORMATION: HCV
<221> NAME/KEY: variation
<222> LOCATION: (2711)...(2711)
<223> OTHER INFORMATION: n = T or C
<221> NAME/KEY: variation
<222> LOCATION: (3644)...(3644)
<223> OTHER INFORMATION: n = A or G

<400> SEQUENCE: 4
atggcgccca tcacggccta ctcccaacag acgcggggcc tacttggttg catcatcact      60
agccttacag gccgggacaa gaaccaggtc gagggagagg ttcaggtggt ttccaccgca     120
acacaatcct tcctggcgac ctgcgtcaac ggcgtgtgtt ggaccgttta ccatggtgct     180
ggctcaaaga ccttagccgg cccaaagggg ccaatcaccc agatgtacac taatgtggac     240
caggacctcg tcggctggca ggcgcccccc ggggcgcgtt ccttgacacc atgcacctgt     300
ggcagctcag acctttactt ggtcacgaga catgctgacg tcattccggt gcgccggcgg     360
ggcgacagta gggggagcct gctctccccc aggcctgtct cctacttgaa gggctcttcg     420
ggtggtccac tgctctgccc ttcggggcac gctgtgggca tcttccggc tgccgtatgc     480 acccgggggg ttgcgaaggc ggtggacttt gtgcccgtag agtccatgga aactactatg     540
cggtctccgg tcttcacgga caactcatcc ccccgccg taccgcagac atttcaagtg     600
gcccacctac acgctcccac tggcagcggc aagagtacta agtgccggc tgcatatgca     660 gcccaagggt acaaggtgct cgtcctcaat ccgtccgttg ccgctacctt agggtttggg     720
gcgtatatgt ctaaggcaca cggtattgac cccaacatca gaactggggt aaggaccatt     780
accacaggcg cccccgtcac atactctacc tatggcaagt tccttgccga tggtggttgc     840
tctgggggcg cttatgacat cataatatgt gatgagtgcc attcaactga ctcgactaca     900
atcttgggca tcggcacagt cctggaccaa gcggagacgg ctggagcgcg gcttgtcgtg     960
ctcgccaccg ctacgcctcc gggatcggtc accgtgccac acccaaacat cgaggaggtg    1020
gccctgtcta atactggaga gatcccctc tatggcaaag ccatccccat tgaagccatc    1080
agggggggaa ggcatctcat tttctgtcat tccaagaaga gtgcgacga gctcgccgca    1140 aagctgtcag gcctcggaat caacgctgtg gcgtattacc gggggctcga tgtgtccgtc    1200
ataccaacta tcggagacgt cgttgtcgtg gcaacagacg ctctgatgac gggctatacg    1260
ggcgactttg actcagtgat cgactgtaac acatgtgtca cccagacagt cgacttcagc    1320
ttggatccca ccttcaccat tgagacgacg accgtgcctc aagacgcagt gtcgcgctcg    1380
cagcggcggg gtaggactgg cagaggtagg atgggcatct acaggtttgt gactccggga    1440
gaacggccct cgggcatgtt cgattcctcg gtcctgtgtg agtgctatga cgcgggctgt    1500
```

```
gcttggtacg agctcacccc cgccgagacc tcggttaggt tgcgggccta cctgaacaca    1560
ccagggttgc ccgtttgcca ggaccacctg gagttctggg agagtgtctt cacaggcctc    1620
acccacatag atgcacactt cttgtcccag accaagcagg caggagacaa cttcccctac    1680
ctggtagcat accaagccac ggtgtgcgcc agggctcagg ccccacctcc atcatgggat    1740
caaatgtgga agtgtctcat acggctgaaa cctacgctgc acgggccaac acccttgctg    1800
tacaggctgg gagccgtcca aaatgaggtc accctcaccc accccataac caaatacatc    1860
atggcatgca tgtcggctga cctggaggtc gtcactagca cctgggtgct ggtgggcgga    1920
gtccttgcag ctctggccgc gtattgcctg acaacaggca gtgtggtcat tgtgggtagg    1980
attatcttgt ccgggaggcc ggctattgtt cccgacaggg agtttctcta ccaggagttc    2040
gatgaaatgg aagagtgcgc ctcgcacctc ccttacatcg agcagggaat gcagctcgcc    2100
gagcaattca agcagaaagc gctcgggtta ctgcaaacag ccaccaaaca agcggaggct    2160
gctgctcccg tggtggagtc caagtggcga gcccttgaga cattctgggc gaagcacatg    2220
tggaatttca tcagcgggat acagtactta gcaggcttat ccactctgcc tgggaacccc    2280
gcaatagcat cattgatggc attcacagcc tctatcacca gcccgctcac cacccaaagt    2340
accctcctgt ttaacatctt gggggggtgg gtggctgccc aactcgcccc cccagcgcc    2400 gcttcggctt tcgtgggcgc cggcatcgcc ggtgcggctg ttggcagcat aggccttggg    2460
aaggtgcttg tggacattct ggcgggttat ggagcaggag tggccggcgc gctcgtggcc    2520
ttcaaggtca tgagcggcga gatgccctcc accgaggacc tggtcaatct acttcctgcc    2580
atcctctctc ctggcgccct ggtcgtcggg gtcgtgtgtg cagcaatact gcgtcgacac    2640
gtgggtccgg gagaggggc tgtgcagtgg atgaaccggc tgatagcgtt cgcctcgcgg    2700
ggtaatcatg nttcccccac gcactatgtg cctgagagcg acgccgcagc gcgtgttact    2760
cagatcctct ccagccttac catcactcag ctgctgaaaa ggctccacca gtggattaat    2820
gaagactgct ccacaccgtg ttccggctcg tgctaaggg atgtttggga ctggatatgc    2880
acggtgttga ctgacttcaa gacctggctc cagtccaagc tcctgccgca gctaccggga    2940 gtccctttt tctcgtgcca acgcgggtac aagggagtct ggcggggaga cggcatcatg    3000
caaaccacct gcccatgtgg agcacagatc accggacatg tcaaaaacgg ttccatgagg    3060
atcgtcgggc ctaagacctg cagcaacacg tggcatggaa cattccccat caacgcatac    3120
accacgggcc cctgcacacc ctctccagcg ccaaactatt ctagggcgct gtggcgggtg    3180
gccgctgagg agtacgtgga ggtcacgcgg gtgggggatt ccactacgt gacgggcatg    3240 accactgaca acgtaaagtg cccatgccag gttccggctc ctgaattctt cacggaggtg    3300
gacggagtgc ggttgcacag gtacgctccg gcgtgcaggc ctctcctacg ggaggaggtt    3360
acattccagg tcgggctcaa ccaatacctg gttgggtcac agctaccatg cgagcccgaa    3420
ccggatgtag cagtgctcac ttccatgctc accgaccct cccacatcac agcagaaacg    3480
gctaagcgta ggttggccag ggggtctccc cctccttgg ccagctcttc agctatccag    3540
ttgtctgcgc cttccttgaa ggcgacatgc actaccacc atgtctctcc ggacgctgac    3600
ctcatcgagg ccaacctcct gtggcggcag agatgggcg ggancatcac ccgcgtggag    3660
tcggagaaca aggtggtagt cctggacttt ttcgacccgc ttcgagcgga ggaggatgag    3720
agggaagtat ccgttccggc ggagatcctg cggaaatcca agaagttccc cgcagcgatg    3780
cccatctggg cgcgcccgga ttacaaccct ccactgttag agtcctggaa ggaccccgac    3840
tacgtccctc cggtggtgca cgggtgcccg ttgccaccta tcaaggcccc tccaatacca    3900
```

```
cctccacgga gaaagaggac ggttgtccta acagagtcct ccgtgtcttc tgccttagcg    3960
gagctcgcta ctaagacctt cggcagctcc gaatcatcgg ccgtcgacag cggcacggcg    4020
accgcccttc ctgaccaggc ctccgacgac ggtgacaaag gatccgacgt tgagtcgtac    4080
tcctccatgc ccccccttga gggggaaccg ggggacccccg atctcagtga cgggtcttgg    4140
tctaccgtga gcgaggaagc tagtgaggat gtcgtctgct gc                        4182
```

```
<210> SEQ ID NO 5
<211> LENGTH: 34
<212> TYPE: DNA
<213> ORGANISM: Artificial Sequence
<220> FEATURE:
<223> OTHER INFORMATION: Chemically synthesized

<400> SEQUENCE: 5
aaaaaaaaaa aaaaaaaaaa aaaaaaaaaa aaaa                                 34

<210> SEQ ID NO 6
<211> LENGTH: 23
<212> TYPE: DNA
<213> ORGANISM: Artificial Sequence
<220> FEATURE:
<223> OTHER INFORMATION: chemically synthesized

<400> SEQUENCE: 6
atggagaaga aggtcattgt gtg                                             23

<210> SEQ ID NO 7
<211> LENGTH: 23
<212> TYPE: DNA
<213> ORGANISM: Artificial Sequence
<220> FEATURE:
<223> OTHER INFORMATION: chemically synthesized

<400> SEQUENCE: 7
gctcccatta ctgcctacac tca                                             23

<210> SEQ ID NO 8
<211> LENGTH: 21
<212> TYPE: DNA
<213> ORGANISM: Artificial Sequence
<220> FEATURE:
<223> OTHER INFORMATION: chemically synthesized

<400> SEQUENCE: 8
ccgctctacc gagcggggag t                                               21

<210> SEQ ID NO 9
<211> LENGTH: 25
<212> TYPE: DNA
<213> ORGANISM: Artificial Sequence
<220> FEATURE:
<223> OTHER INFORMATION: chemically synthesized

<400> SEQUENCE: 9
ctctcctcaa gcgtattcaa caagg                                           25

<210> SEQ ID NO 10
<211> LENGTH: 25
<212> TYPE: DNA
<213> ORGANISM: Artificial Sequence
<220> FEATURE:
<223> OTHER INFORMATION: chemically synthesized

<400> SEQUENCE: 10
```

-continued ccgtgcagcg taggtttcag ccgta					25

<210> SEQ ID NO 11
<211> LENGTH: 24
<212> TYPE: DNA
<213> ORGANISM: Artificial Sequence
<220> FEATURE:
<223> OTHER INFORMATION: chemically synthesized

<400> SEQUENCE: 11
cccattgtat gggatctgat ctgg					24

<210> SEQ ID NO 12
<211> LENGTH: 28
<212> TYPE: DNA
<213> ORGANISM: Artificial Sequence
<220> FEATURE:
<223> OTHER INFORMATION: chemically synthesized

<400> SEQUENCE: 12
caagctgaag tcgactgtct gggtgaca					28

<210> SEQ ID NO 13
<211> LENGTH: 29
<212> TYPE: DNA
<213> ORGANISM: Artificial Sequence
<220> FEATURE:
<223> OTHER INFORMATION: chemically synthesized

<400> SEQUENCE: 13
tacttggtca cgagacatgc tgacgtcat					29

<210> SEQ ID NO 14
<211> LENGTH: 19
<212> TYPE: DNA
<213> ORGANISM: Artificial Sequence
<220> FEATURE:
<223> OTHER INFORMATION: chemically synthesized

<400> SEQUENCE: 14
ggagaggata gcagggagt					19

<210> SEQ ID NO 15
<211> LENGTH: 29
<212> TYPE: DNA
<213> ORGANISM: Artificial Sequence
<220> FEATURE:
<223> OTHER INFORMATION: chemically synthesized

<400> SEQUENCE: 15
cgtatatgtc taaggcacac ggtattgac					29

<210> SEQ ID NO 16
<211> LENGTH: 28
<212> TYPE: DNA
<213> ORGANISM: Artificial Sequence
<220> FEATURE:
<223> OTHER INFORMATION: chemically synthesized

<400> SEQUENCE: 16
ggctggtgat agaggctgtg aatgccat					28

<210> SEQ ID NO 17
<211> LENGTH: 28
<212> TYPE: DNA
<213> ORGANISM: Artificial Sequence
<220> FEATURE:

<223> OTHER INFORMATION: chemically synthesized

<400> SEQUENCE: 17
ggatcaaatg tggaagtgtc tcatacgg                                              28

<210> SEQ ID NO 18
<211> LENGTH: 19
<212> TYPE: DNA
<213> ORGANISM: Artificial Sequence
<220> FEATURE:
<223> OTHER INFORMATION: chemically synthesized

<400> SEQUENCE: 18
tcgaggttgt ggagtacac                                                        19

<210> SEQ ID NO 19
<211> LENGTH: 29
<212> TYPE: DNA
<213> ORGANISM: Artificial Sequence
<220> FEATURE:
<223> OTHER INFORMATION: chemically synthesized

<400> SEQUENCE: 19
gcaatagcat cattgatggc attcacagc                                             29

<210> SEQ ID NO 20
<211> LENGTH: 20
<212> TYPE: DNA
<213> ORGANISM: Artificial Sequence
<220> FEATURE:
<223> OTHER INFORMATION: chemically synthesized

<400> SEQUENCE: 20
ggcctcgatg aggtcagcgt                                                       20

<210> SEQ ID NO 21
<211> LENGTH: 25
<212> TYPE: DNA
<213> ORGANISM: Artificial Sequence
<220> FEATURE:
<223> OTHER INFORMATION: chemically synthesized

<400> SEQUENCE: 21
ctctcctcaa gcgtattcaa caagg                                                 25

<210> SEQ ID NO 22
<211> LENGTH: 20
<212> TYPE: DNA
<213> ORGANISM: Artificial Sequence
<220> FEATURE:
<223> OTHER INFORMATION: chemically synthesized

<400> SEQUENCE: 22
gtaaagtgcc cgtgtcaggt                                                       20

<210> SEQ ID NO 23
<211> LENGTH: 21
<212> TYPE: DNA
<213> ORGANISM: Artificial Sequence
<220> FEATURE:
<223> OTHER INFORMATION: chemically synthesized

<400> SEQUENCE: 23
catgatagtt gtgtcaattg g                                                     21

<210> SEQ ID NO 24

```
<211> LENGTH: 19
<212> TYPE: DNA
<213> ORGANISM: Artificial Sequence
<220> FEATURE:
<223> OTHER INFORMATION: chemically synthesized

<400> SEQUENCE: 24
gtctaccgtg agcgaggaa                                           19

<210> SEQ ID NO 25
<211> LENGTH: 21
<212> TYPE: DNA
<213> ORGANISM: Artificial Sequence
<220> FEATURE:
<223> OTHER INFORMATION: chemically synthesized

<400> SEQUENCE: 25
atactcctgg acagggcccc t                                        21

<210> SEQ ID NO 26
<211> LENGTH: 36
<212> TYPE: DNA
<213> ORGANISM: Artificial Sequence
<220> FEATURE:
<223> OTHER INFORMATION: chemically synthesized

<400> SEQUENCE: 26
gcgcgcgcat cgatcgggga gtaaaaagat gcctac                        36

<210> SEQ ID NO 27
<211> LENGTH: 783
<212> TYPE: DNA
<213> ORGANISM: Artificial Sequence
<220> FEATURE:
<223> OTHER INFORMATION: HCV

<400> SEQUENCE: 27
gcctccaaag ccgccctcat tgaggaaggg cagcggatgg cggagatgct caaatctaag      60
atacaaggcc tcctacaaca ggccacaagg caagctcaag acatacagcc agctatacag     120
tcatcatggc caagcttga acaattttgg gccaaacaca tgtggaactt catcagtggt      180
atacagtacc tagcaggact ctccacccta ccgggaaatc ctgcagtagc atcaatgatg     240
gcttttagcg ccgcgctgac tagcccacta cccaccagca ccaccatcct cttgaacatc     300
atgggaggat ggttggcctc tcagattgcc ccccctgccg gagccactgg cttcgttgtc     360
agtggtctag tggggcggc cgtcggaagc ataggcctgg gtaagatact ggtgacgtt      420 ttggccgggt acggcgcagg catttcaggg gccctcgtag cttttaagat catgagcggc     480
gagaagccca cggtagaaga cgttgtgaat ctcctgcctg ctattctgtc tcctggtgcg     540
ttggtagtgg gagtcatctg tgcagcaatc ctgcgtcgac acgtgggtcc gggagagggg     600
gctgtgcagt ggatgaaccg gctgatagcg ttcgcctcgc ggggtaatca tgcttccccc     660
acgcactatg tgcctgagag cgacgccgca gcgcgtgtta ctcagatcct ctccagcctt     720
accatcactc agctgctgaa aaggctccac cagtggatta tgaagactg ctccacaccg      780 tgt                                                                   783

<210> SEQ ID NO 28
<211> LENGTH: 261
<212> TYPE: PRT
<213> ORGANISM: Artificial Sequence
<220> FEATURE:
<223> OTHER INFORMATION: HCV
```

```
<400> SEQUENCE: 28

Ala Ser Lys Ala Ala Leu Ile Glu Glu Gly Gln Arg Met Ala Glu Met
 1               5                  10                  15

Leu Lys Ser Lys Ile Gln Gly Leu Leu Gln Gln Ala Thr Arg Gln Ala
                20                  25                  30

Gln Asp Ile Gln Pro Ala Ile Gln Ser Ser Trp Pro Lys Leu Glu Gln
             35                  40                  45

Phe Trp Ala Lys His Met Trp Asn Phe Ile Ser Gly Ile Gln Tyr Leu
         50                  55                  60

Ala Gly Leu Ser Thr Leu Pro Gly Asn Pro Ala Val Ala Ser Met Met
65                  70                  75                  80

Ala Phe Ser Ala Ala Leu Thr Ser Pro Leu Pro Thr Ser Thr Thr Ile
                85                  90                  95

Leu Leu Asn Ile Met Gly Gly Trp Leu Ala Ser Gln Ile Ala Pro Pro
                100                 105                 110

Ala Gly Ala Thr Gly Phe Val Val Ser Gly Leu Val Gly Ala Ala Val
                115                 120                 125

Gly Ser Ile Gly Leu Gly Lys Ile Leu Val Asp Val Leu Ala Gly Tyr
    130                 135                 140

Gly Ala Gly Ile Ser Gly Ala Leu Val Ala Phe Lys Ile Met Ser Gly
145                 150                 155                 160

Glu Lys Pro Thr Val Glu Asp Val Val Asn Leu Leu Pro Ala Ile Leu
                165                 170                 175

Ser Pro Gly Ala Leu Val Val Gly Val Ile Cys Ala Ala Ile Leu Arg
            180                 185                 190

Arg His Val Gly Pro Gly Glu Gly Ala Val Gln Trp Met Asn Arg Leu
        195                 200                 205

Ile Ala Phe Ala Ser Arg Gly Asn His Ala Ser Pro Thr His Tyr Val
    210                 215                 220

Pro Glu Ser Asp Ala Ala Ala Arg Val Thr Gln Ile Leu Ser Ser Leu
225                 230                 235                 240

Thr Ile Thr Gln Leu Leu Lys Arg Leu His Gln Trp Ile Asn Glu Asp
                245                 250                 255

Cys Ser Thr Pro Cys
                260
```